(12) United States Patent
Fernandez Prieto et al.

(10) Patent No.: US 8,207,107 B2
(45) Date of Patent: *Jun. 26, 2012

(54) DI-AMIDO GELLANT FOR USE IN CONSUMER PRODUCT COMPOSITIONS

(75) Inventors: Susana Fernandez Prieto, Benicarlo-Castellon (ES); Johan Smets, Lubbeek (BE); Beatriu Escuder Gil, Sant Mateu-Castello (ES); Juan Felipe Miravet Celades, Castellon (ES); Vincent Josep Nebot Carda, Vila real-Castellon (ES)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/045,659

(22) Filed: Mar. 11, 2011

(65) Prior Publication Data

US 2011/0224455 A1 Sep. 15, 2011

(30) Foreign Application Priority Data

Mar. 12, 2010 (EP) .................................... 10156371

(51) Int. Cl.
*C11D 7/26* (2006.01)
*C11D 7/32* (2006.01)

(52) U.S. Cl. ..................... 510/501; 564/152; 564/153

(58) Field of Classification Search ............ 510/501; 564/152, 153
See application file for complete search history.

(56) References Cited

U.S. PATENT DOCUMENTS

| 5,707,952 | A | 1/1998 | Lambremont et al. |
| 7,018,642 | B2 | 3/2006 | Degenhardt et al. |
| 7,332,529 | B2 * | 2/2008 | Carr ................................ 516/20 |
| 7,534,915 | B2 | 5/2009 | van Bommel et al. |
| 7,708,982 | B2 | 5/2010 | O'Leary et al. |
| 7,910,526 | B2 | 3/2011 | Kakizaki et al. |
| 2004/0247664 | A1 | 12/2004 | Dreja et al. |
| 2006/0089416 | A1 | 4/2006 | Carr |
| 2008/0057005 | A1 | 3/2008 | Lehn et al. |
| 2008/0096780 | A1 | 4/2008 | Veugelers et al. |

FOREIGN PATENT DOCUMENTS

| GB | 1352536 | 3/1972 |
| WO | WO 97/17963 A1 | 5/1997 |

OTHER PUBLICATIONS

Barnes, D.J.; Chapman, R.L.; Vagg, R.S.; Watton, E.C., J. Chem. Eng. Data 1978, 23(4), 349-350.
Moll, Maria. Acta Pol. Pharm: 1968, 25(4), 367-373 (Pol).
Sukuzi, M. Tetrahedron Letters, Elsevier, Amsterdam 45 (2004) 5399-5402.
Estroff, Lara; Hamilton, Andrew;Chemical Reviews, vol. 104, No. 3, Jan. 1, 2004, 1201-1218.
International Search report dated Mar. 11, 2011 containing 7 pages.
International Search Report dated Mar. 11, 2011 containing 7 pages for U.S. Appl. No. 13/045,577.
Becerril, J.;Bolte, M.; Burguete, M.I.; Galindo, F.; Garcia-Espana, E.; Luis, S. V.; Miravet J. F. J Am. Chem. Soc. 2003, 125, 6677-6686.
U.S. Appl. No. 13/045,577, filed Mar. 11, 2011, Susana Fernandez-Prieto, et al.
U.S. Appl. No. 13/045,749, filed Mar. 11, 2011, Susana Fernandez-Prieto, et al.
U.S. Appl. No. 13/045,768, filed Mar. 11, 2011, Susana Fernandez-Prieto, et al.

* cited by examiner

*Primary Examiner* — Gregory Delcotto
(74) *Attorney, Agent, or Firm* — Melissa G. Krasovec; Leonard W. Lewis; Steven W. Miller

(57) ABSTRACT

The invention is to di-amido gellant that are suitable for use in consumer product compositions.

4 Claims, 1 Drawing Sheet

DI-AMIDO GELLANT FOR USE IN CONSUMER PRODUCT COMPOSITIONS

FIELD OF THE INVENTION

The present invention relates to structurants that are compatible with a broad range of consumer products, including detergent compositions, and do not affect product clarity.

BACKGROUND OF THE INVENTION

It has long been desired to create a broad range of variants, offering unique benefits, from a single base detergent composition. By adding specific benefit agents to such a base, one could simply and cost-effectively provide compositions that are tailored to a specific group of users. However, a big challenge is to find structurants to thicken such compositions which are compatible with a broad range of potential detergent ingredients.

External structurants for providing rheological benefits to consumer product compositions are known. Examples of desired benefits of such structurants include particle suspension, shear thinning properties, a thick appearance on the shelf, as well as stabilization of other materials which are desired to be incorporated within the composition. Known external structurants include those derived from castor oil, fatty acids, fatty esters, or fatty soap water-insoluble waxes. However, their applicability for detergent applications is limited due to degradation by conventional detergent ingredients such as enzymes, including protease and lipase (lipase hydrolyses ester bonds present in castor oil derivatives), which are desirable for improved low temperature cleaning. This class of structurants is also incompatible with low pH and peroxide bleaches. Such external structurants make the detergent compositions less aesthetically pleasing since they impart additional cloudiness and hence reduce the clarity of the composition. For these reasons, formulators have often resorted to polymeric structurants. However, they can result in a stringy pour profile that is undesirable to the consumer, particularly when "gel-like" viscosities are desired.

As such, a need remains for a structurant that is compatible with a broad range of detergent compositions, that does not affect product clarity, while still providing good structuring of the detergent ingredients and being easy to pour.

SUMMARY OF THE INVENTION

The present invention is to a di-amido gellant having the following formula:

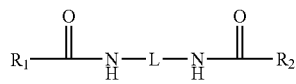

[I]

wherein: $R_1$ and $R_2$ are aminofunctional end-groups which may be the same or different, and L is a linking moiety of molecular weight from 14 to 500 g/mol, and with the exclusion that the di-amido gellant is not a protein.

Another aspect of the present invention relates to the use of such di-amido gellants for structuring consumer product compositions, preferably fluid detergent compositions.

DETAILED DESCRIPTION OF THE INVENTION

Figure 1:
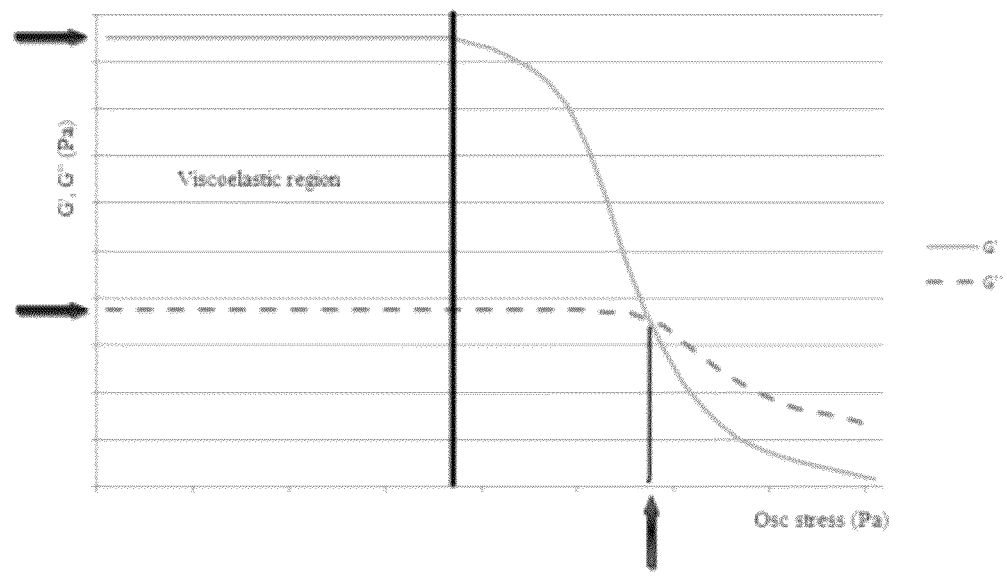
FIG. 1 details G' and G" within the linear viscoelastic region and the oscillation stress at the point where G' and G" cross over as a measure for gel strength.

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

The di-amido gellants are particularly useful for consumer product compositions having a fluid form, particularly liquid and gel forms. Such fluid forms also include fluid detergent compositions. Fluid detergent compositions as described herein include but are not limited to consumer products such as: shampoos; skin cleaners and exfolients; shaving liquids, foams and gels; products for treating fabrics, hard surfaces and any other surfaces in the area of fabric and home care, including: dishwashing, laundry cleaning, laundry and rinse additives, hard surface cleaning including floor and toilet bowl cleaners; products relating to oral care including toothpastes and gels and whiteners. A particularly preferred fluid detergent composition is a "fluid laundry detergent composition". As used herein, "fluid laundry detergent composition" refers to any laundry treatment composition comprising a fluid capable of wetting and cleaning fabric e.g., clothing, in a domestic washing machine.

The consumer product composition can include solids or gases in suitably subdivided form, but the overall composition excludes product forms which are non-fluid overall, such as tablets or granules. The consumer product compositions preferably have densities in the range from of 0.9 to 1.3 grams per cubic centimeter, more preferably from 1.00 to 1.10 grams per cubic centimeter, excluding any solid additives but including any bubbles, if present.

The consumer product compositions may be opaque, semi-transparent or even clear. When clarity of the consumer product composition is desired, the consumer product composition has a turbidity of from 5 NTU to less than 3000 NTU, preferably less than 1000 NTU, more preferably less than 500 NTU and most preferably less than 100 NTU.

All percentages, ratios and proportions used herein are by weight percent of the composition, unless otherwise specified. All average values are calculated "by weight" of the composition or components thereof, unless otherwise expressly indicated.

External Structurant:

The external structurant preferably imparts a shear thinning viscosity profile to the consumer product composition, independently from, or extrinsic from, any structuring effect of the detersive surfactants of the composition. Preferred external structurants include those which provide a pouring viscosity from 50 cps to 20,000 cps, more preferably from 200 cps to 10,000 cps, most preferably from 500 cps to 7,000 cps. The consumer product composition preferably has a resting viscosity of at least 1,500 cps, preferably at least 10,000 cps, more preferably at least 50,000 cps. This resting (low stress) viscosity represents the viscosity of the consumer product composition under gentle shaking in the package and during transportation. Alternatively, the consumer product composition may be a thixotropic gel. Such compositions may have a resting viscosity of from 10,000 cps to 500,000 cps, preferably from 100,000 cps to 400,000 cps, more preferably from 200,000 to 300,000. The preferred shear-thinning characteristics of the consumer product is defined as a ratio of low stress viscosity to pouring viscosity of at least 2, preferably at least 10, more preferably at least 100, up to 2000.

The pouring viscosity is measured at a shear rate of 20 $sec^{-1}$, which is a shear rate that the consumer product composition is typically exposed to during pouring. The resting (low stress) viscosity is determined under a constant stress of 0.1 Pa during a viscosity creep experiment over a 5 minute interval. Rheology measurements over the 5 minute interval are made after the composition has rested at zero shear rate for at least 10 minutes, between loading the sample in the rheometer and running the test. The data over the last 3 minutes are used to fit a straight line, and from the slope of this line, the low stress viscosity is calculated. The viscosity is measured at 21° C. using a TA AR 2000 (or AR G2) rheometer with a 40 mm stainless steel plate having a gap of 500 microns.

1. Di-Amido Gellant

The consumer product composition includes a di-amido gellant as an external structurant at a level from 0.01 wt % to 10 wt %, preferably from 0.05 wt % to 5 wt %, more preferably from 0.1 wt % to 2 wt %, most preferably from 0.4 wt % to 1 wt %. In an alternative embodiment, the consumer product composition comprises from 0.1 wt % to 0.5 wt % of the di-amido gallant.

The di-amido gellant comprises at least two nitrogen atoms, wherein at least two of said nitrogen atoms form amido functional substitution groups. In one embodiment, the amido groups are different. In a preferred embodiment, the amido functional groups are the same. The di-amido gellant has the following formula:

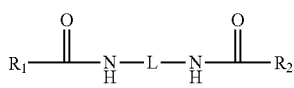
[I]

wherein: $R_1$ and $R_2$ are aminofunctional end-groups which may be the same or different and L is a linking moeity of molecular weight from 14 to 500 g/mol.

In a preferred embodiment: $R_1$ is $R_3$ or

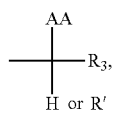

and $R_2$ is $R_4$ or

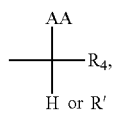

wherein AA is selected from the group consisting of:

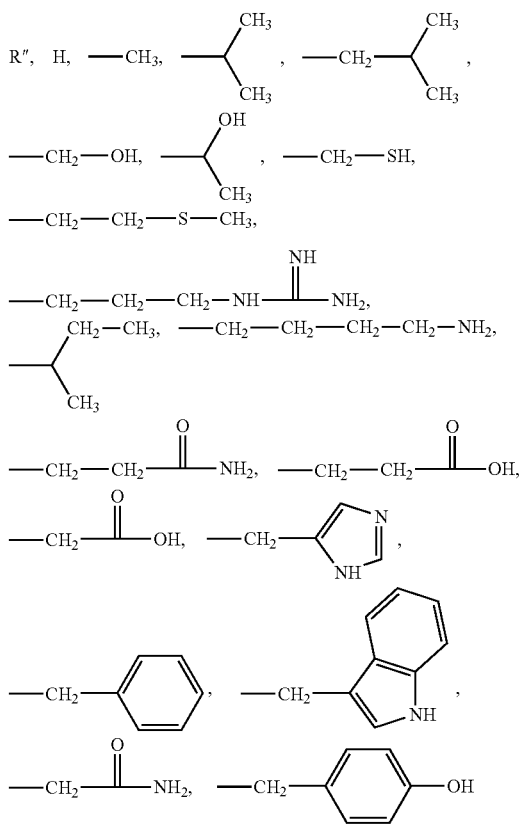

and $R_3$ and $R_4$ independently have the formula:

$(L')_m\text{-}(L'')_q\text{—R}$, where $(m+q)$ is from 1 to 10, [II]

such that $R_1$ and $R_2$ are aminofunctional end-groups.
Preferably, L has the formula:

$A_a\text{-}B_b\text{-}C_c\text{-}D_d$, where $(a+b+c+d)$ is from 1 to 20, [III]

wherein L', L" from formula [II] and A, B, C, D from formula [III] are independently selected from the group consisting of:

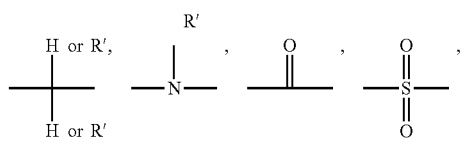

-continued
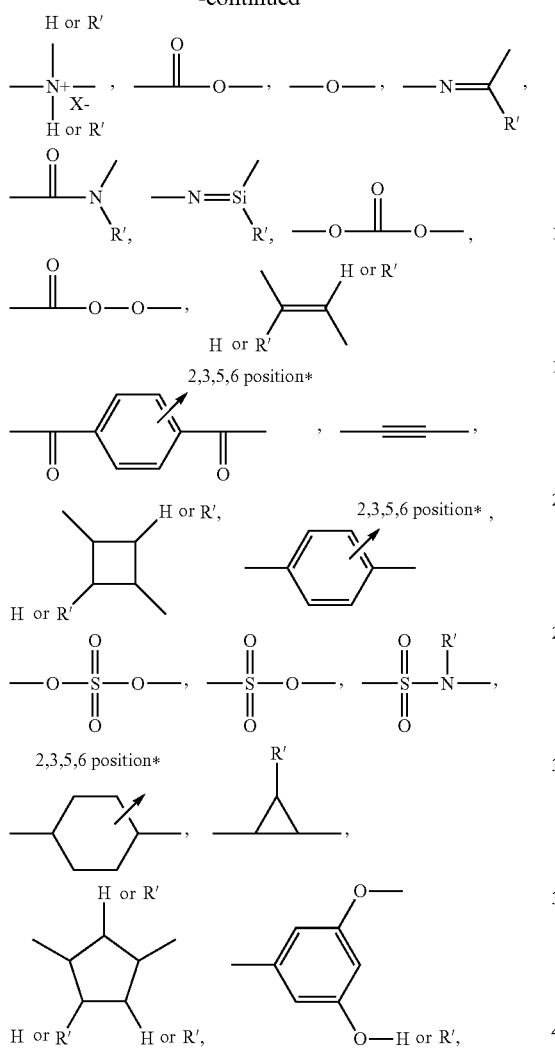
Preferably, L″ from formula [II] and A, B, C, D from formula [III] are independently selected from the group consisting of:
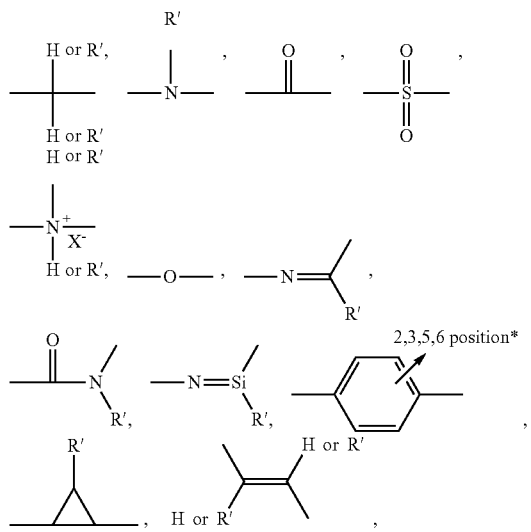
-continued
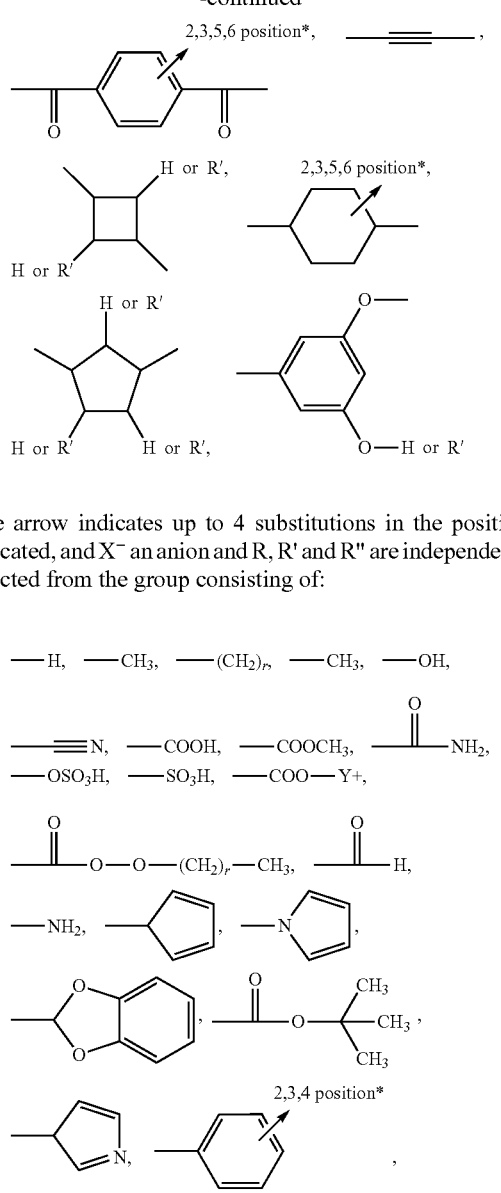
*the arrow indicates up to 4 substitutions in the positions indicated, and $X^-$ an anion and R, R′ and R″ are independently selected from the group consisting of:
—H, —CH$_3$, —(CH$_2$)$_r$—CH$_3$, —OH,
≡N, —COOH, —COOCH$_3$, —C(O)—NH$_2$,
—OSO$_3$H, —SO$_3$H, —COO—Y+,
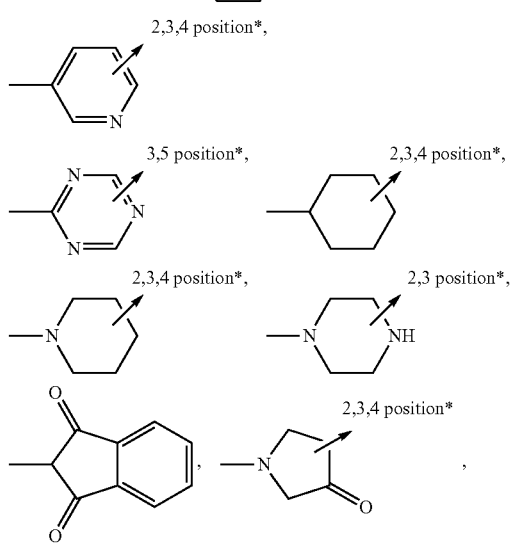

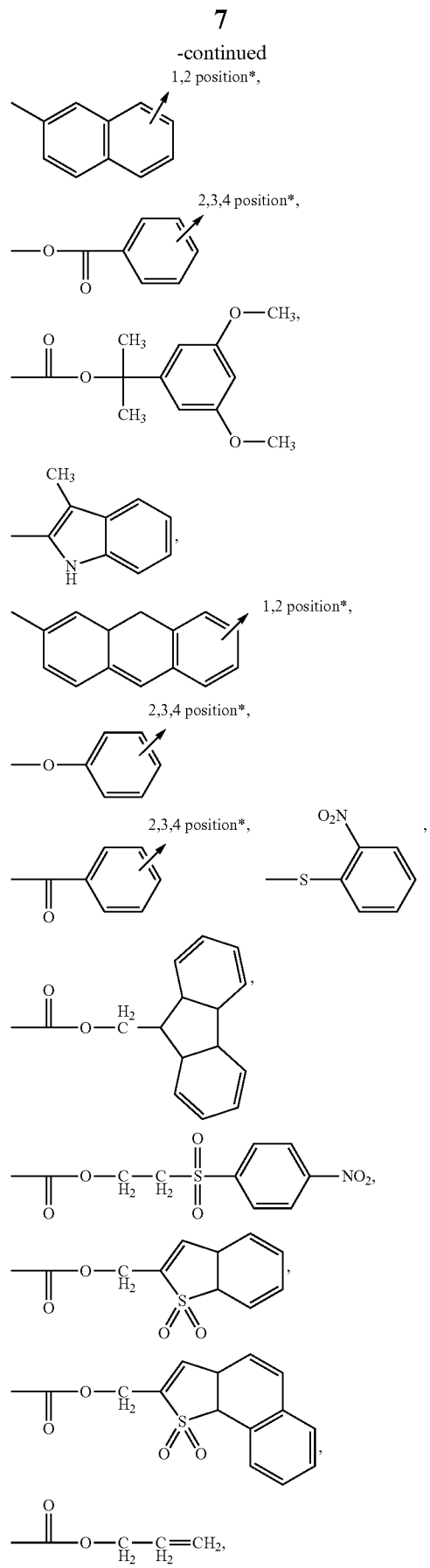
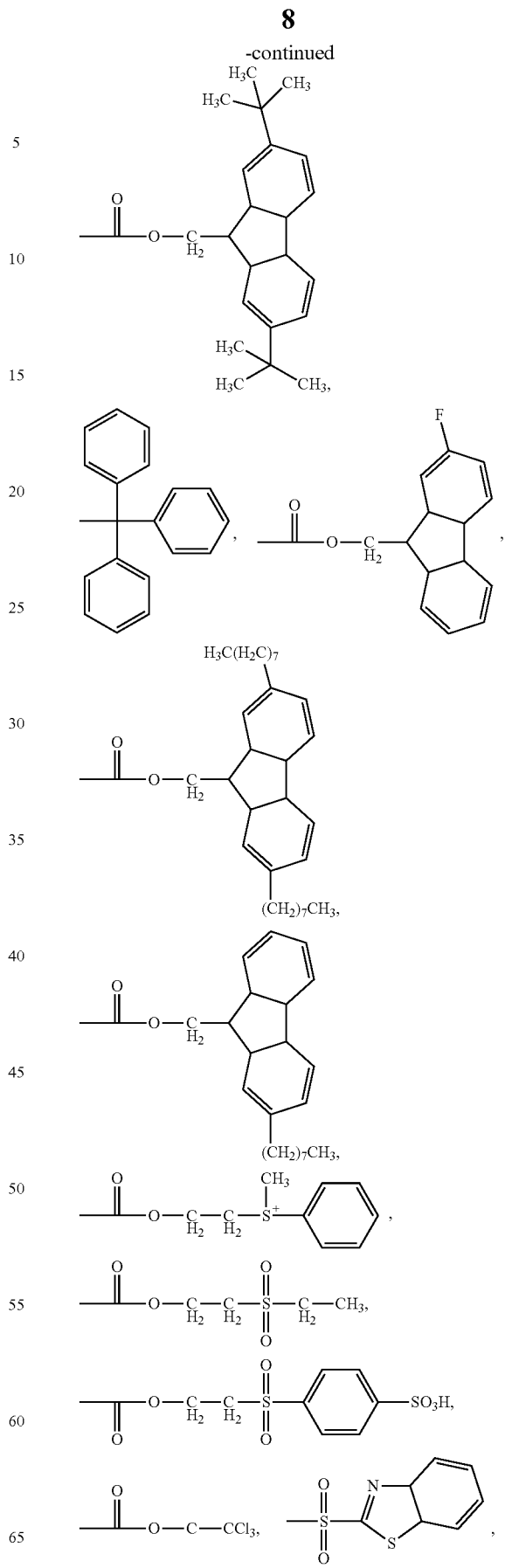

9

-continued

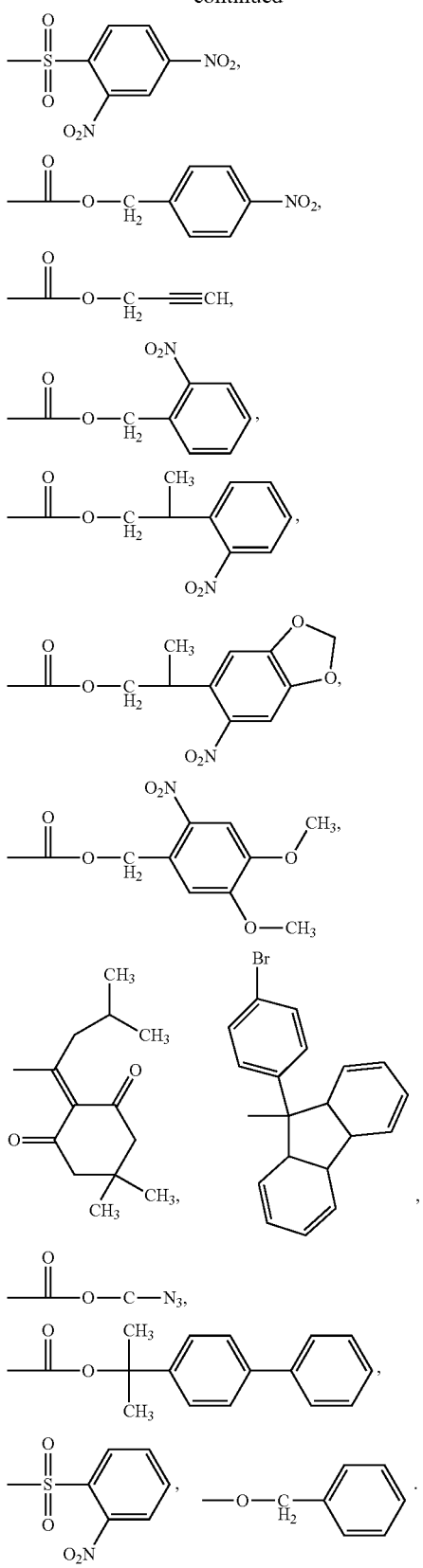

Preferably, R, R' and R" are independently selected from the group consisting of:

10

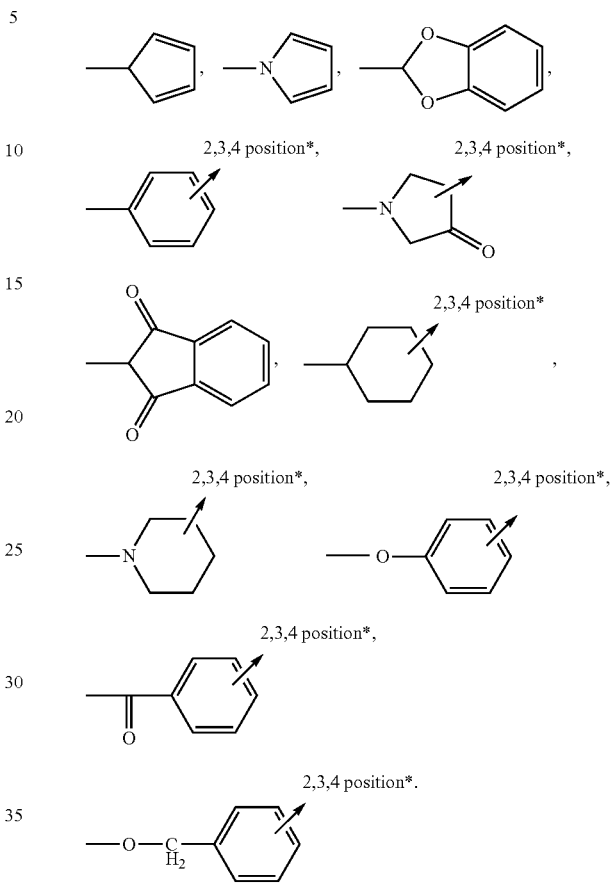

*the arrow indicates up to 4 substitutions in the positions indicated, r is an integer from 1 to 20 and r is a cation.

In a more preferred embodiment, the di-amido gellant is characterized in that:

L is an aliphatic linking group with a backbone chain of from 2 to 20 carbon atoms, preferably —$(CH_2)_n$— wherein n is selected from 2 to 20, and $R_1$ and $R_2$ both have the structure:

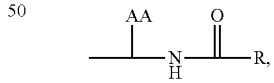

wherein: AA is selected from the group consisting of:

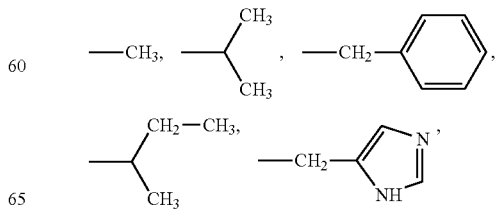

or from the group consisting of:

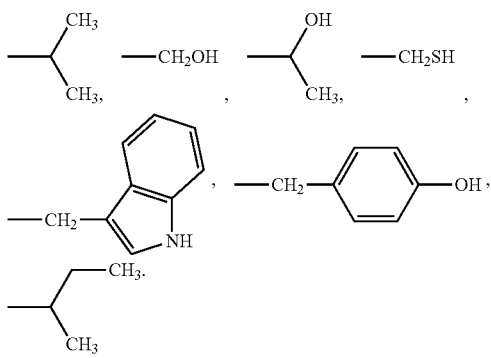

and R is selected from the group:

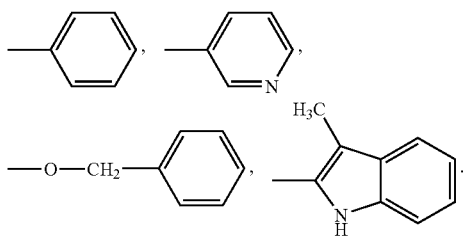

or from the group:

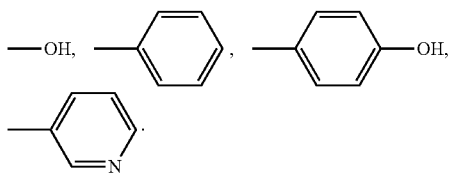

In another embodiment R, R' and R" can independently be selected from the group consisting of: an ethoxy group, an epoxy group with 1 to 15 ethoxy or epoxy units. In another embodiment, the R, R' and R" may comprise a functional end group selected from the group consisting of: an aromatic, alicyclic, heteroaromatic, heterocyclic group including mono-, di-, and oligo-polysaccharides.

Preferably, L is selected from C2 to C20 hydrocarbyl chains, preferably C6 to C12, more preferably C8 to C10. Preferably, the di-amido gellant has a molecular weight from 150 to 1500 g/mol, more preferably from 300 g/mol to 900 g/mol, most preferably from 400 g/mol to 700 g/mol.

In another embodiment, two or more of L, L' and L" are the same group. The di-amido gellant molecule can be symmetric with respect to the L entity or can be asymmetric. Without intending to be bound by theory, it is believed that symmetric di-amido gellant molecules allow for more orderly structured networks to form whereas compositions comprising one or more asymmetric di-amido gellant molecules can create disordered networks. The types of interactions between the di-amido gellant molecules are described in detail hereinafter.

In one embodiment, the AA comprises at least one of: Alanine, β-Alanine and substituted Alanines; Linear Amino-Alkyl Carboxylic Acid; Cyclic Amino-Alkyl Carboxylic Acid; Aminobenzoic Acid Derivatives; Aminobutyric Acid Derivatives; Arginine and Homologues; Asparagine; Aspartic Acid; p-Benzoyl-Phenylalanine; Biphenylalanine; Citrulline; Cyclopropylalanine; Cyclopentylalanine; Cyclohexylalanine; Cysteine, Cystine and Derivatives; Diaminobutyric Acid Derivatives; Diaminopropionic Acid; Glutamic Acid Derivatives; Glutamine; Glycine; Substituted Glycines; Histidine; Homoserine; Indole Derivatives; Isoleucine; Leucine and Derivatives; Lysine; Methionine; Naphthylalanine; Norleucine; Norvaline; Ornithine; Phenylalanine; Ring-Substituted Phenylalanines; Phenylglycine; Pipecolic Acid, Nipecotic Acid and Isonipecotic Acid; Proline; Hydroxyproline; Thiazolidine; Pyridylalanine; Serine; Statine and Analogues; Threonine; Tetrahydronorharman-3-carboxylic Acid; 1,2,3,4-Tetrahydroisoquinoline; Tryptophane; Tyrosine; Valine; and combinations thereof.

The molecule may also comprise protective groups, preferably from 1 to 2 protective groups, preferably two protective groups. Examples of suitable protective groups are provided in "Protecting Groups", P. J. Kocienski, ISBN 313 135601 4, Georg Thieme Verlag, Stutgart; and "Protective Groups in Organic Chemistry", T. W. Greene, P. G. M. Wuts, ISBN 0-471-62301-6, John Wiley & Sons, Inc, New York. A non-limiting example of a suitable protective group is 9-fluorenylmethoxycarbonyl. N-Benzyloxycarbonyl, N-t-Butyloxycarbonyl.

In one embodiment, the di-amido gellant is a thermoreversible gellant such as described in U.S. Pat. No. 7,332,529. An example of this molecule is provided below:

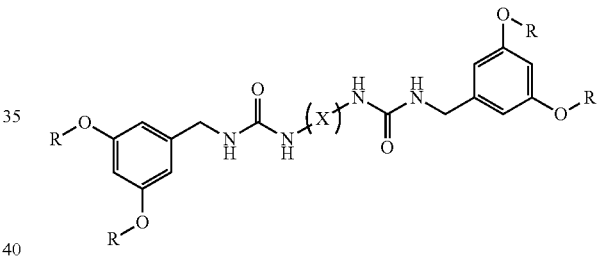

wherein X is C6 to C12 alylene, each R is C9 to C12 alkyl, provided that when X is C6 alkylene, each R must be C10 alkyl. In a preferred embodiment, each R is C10 alkyl. In a more preferred embodiment, each R is C10 alkyl and X is C6 or C12 alkylene. In another embodiment, each R is C12 alkyl. In another preferred embodiment, each R is C12 alkyl and X is C12 alkylene.

The di-amido gellant preferably has a minimum gelling concentration (MGC) of from 0.1 to 100 mg/mL in the consumer product composition, preferably from 0.1 to 25 mg/mL, more preferred from 0.5 to 10 mg/mL in accordance with the MGC Test Method. The MGC as used herein can be represented as mg/ml or as a wt %, where wt % is calculated as the MGC in mg/ml divided by 10. In one embodiment, when measured in the consumer product composition, the MGC is from 0.1 to 100 mg/mL, preferably from 0.1 to 25 mg/mL of said di-amido gellant, more preferably from 0.5 to 10 mg/mL, or at least 0.1 mg/mL, at least 0.3 mg/mL, at least 0.5 mg/mL, at least 1.0 mg/mL, at least 2.0 mg/mL, at least 5.0 mg/mL of di-amido gellant. While consumer product compositions may comprise a di-amido gellant structurant at a concentration either above or below the MGC, the di-amido gellants of the invention result in particularly useful rheologies below the MGC.

Suitable di-amido gellants may be selected from table 2, table 3, table 4 and mixtures thereof. More preferably, the di-amido gellants are selected from table 3, and mixtures thereof. Alternatively, the di-amido gellants are selected from table 4, and mixtures thereof.

To provide more robust structuring, the consumer product may comprise a mixture of two or more di-amido gellant structurants. Such a mixture may include a di-amido gellant structurant which has higher solubility in water and/or non-aminofunctional solvents, with a di-amido gellant with lower solubility in water and/or non-aminofunctional solvents. Without intending to be bound by theory, it is believed that a di-amido gellant that is more soluble in water may have difficulty forming a gel in a cleaning composition at a low level, while one that is less soluble, may have difficulty forming a gel because it will be difficult to solubilize it. Mixtures of these two di-amido gellants at different levels show synergies in the way that the one that is more soluble helps to solubilize the other, allowing both to help structure the composition. For instance, dibenzyl (2S,2'S)-1,1'-(propane-1,3-diylbis(azanediyl))bis(3-methyl-1-oxobutane-2,1-diyl)dicarbamate has improved solubility when incorporated in combination with the more water-soluble N,N'-(2S,2'S)-1,1'-(propane-1,3-diylbis(azanediyl))bis(3-methyl-1-oxobutane-2,1-diyl)diisonicotinamide.

Di-Amido Gellant Examples of Use in the Present Invention:

TABLE 1

Non-limiting examples of di-amido gellants of the invention:

| Amido Bolaform Example | L | $R_1 = R_2$ |
|---|---|---|
| N,N'-(2S,2'S)-1,1'-(hexane-1,6-diylbis(azanediyl))bis(1-oxopropane-2,1-diyl)diisonicotinamide | —(CH$_2$)$_6$— | 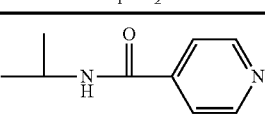 |
| 1,1'-(propane-1,3-diyl)bis(3-phenylurea) | —(CH$_2$)$_3$— | 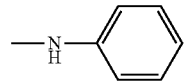 |
| N-N'-(2S,2'S)-1,1'-(dodecane-1,12-diylbis(azanediyl))bis(3-(1H-imidazol-5-yl)-1-oxopropane-2,1-diyl)dibenzamide | —(CH$_2$)$_{12}$— | 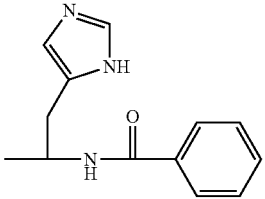 |

TABLE 2

Non-limiting examples of di-amido gellants of the invention:

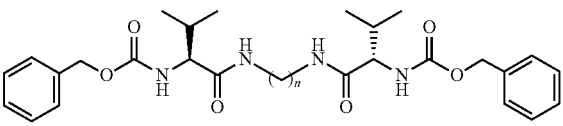

dibenzyl (2S,2'S)-1,1'-(ethane-1,2-diylbis(azanediyl))bis(3-methyl-1-oxobutane-2,1-diyl)dicarbamate
dibenzyl (2S,2'S)-1,1'-(propane-1,3-diylbis(azanediyl))bis(3-methyl-1-oxobutane-2,1-diyl)dicarbamate
dibenzyl (2S,2'S)-1,1'-(butane-1,4-diylbis(azanediyl))bis(3-methyl-1-oxobutane-2,1-diyl)dicarbamate TABLE 2-continued Non-limiting examples of di-amido gellants of the invention:

dibenzyl (2S,2'S)-1,1'-(pentane-1,5-diylbis(azanediyl))bis(3-methyl-1-oxobutane-2,1-diyl)dicarbamate
dibenzyl (2S,2'S)-1,1'-(hexane-1,6-diylbis(azanediyl))bis(3-methyl-1-oxobutane-2,1-diyl)dicarbamate
dibenzyl (2S,2'S)-1,1'-(heptane-1,7-diylbis(azanediyl))bis(3-methyl-1-oxobutane-2,1-diyl)dicarbamate
dibenzyl (2S,2'S)-1,1'-(octane-1,8-diylbis(azanediyl))bis(3-methyl-1-oxobutane-2,1-diyl)dicarbamate
dibenzyl (2S,2'S)-1,1'-(nonane-1,9-diylbis(azanediyl))bis(3-methyl-1-oxobutane-2,1-diyl)dicarbamate
dibenzyl (2S,2'S)-1,1'-(decane-1,10-diylbis(azanediyl))bis(3-methyl-1-oxobutane-2,1-diyl)dicarbamate
dibenzyl (2S,2'S)-1,1'-(undecane-1,11-diylbis(azanediyl))bis(3-methyl-1-oxobutane-2,1-diyl)dicarbamate
dibenzyl (2S,2'S)-1,1'-(dodecane-1,12-diylbis(azanediyl))bis(3-methyl-1-oxobutane-2,1-diyl)dicarbamate
dibenzyl (2S,2'S)-1,1'-(tridecane-1,13-diylbis(azanediyl))bis(3-methyl-1-oxobutane-2,1-diyl)dicarbamate
dibenzyl (2S,2'S)-1,1'-(hexadecane-1,16-diylbis(azanediyl))bis(3-methyl-1-oxobutane-2,1-diyl)dicarbamate
dibenzyl (2S,2'S)-1,1'-(octodecane-1,18-diylbis(azanediyl))bis(3-methyl-1-oxobutane-2,1-diyl)dicarbamate
dibenzyl (2S,2'S)-1,1'-(tetradecane-1,14-diylbis(azanediyl))bis(3-methyl-1-oxobutane-2,1-diyl)dicarbamate

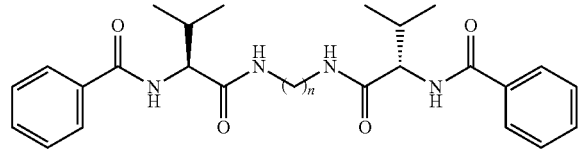

N,N'-(2S,2'S)-1,1'-(ethane-1,2-diylbis(azanediyl))bis(3-methyl-1-oxobutane-2,1-diyl)dibenzamide
N,N'-(2S,2'S)-1,1'-(butane-1,4-diylbis(azanediyl))bis(3-methyl-1-oxobutane-2,1-diyl)dibenzamide
N,N'-(2S,2'S)-1,1'-(propane-1,3-diylbis(azanediyl))bis(3-methyl-1-oxobutane-2,1-diyl)dibenzamide
N,N'-(2S,2'S)-1,1'-(hexane-1,6-diylbis(azanediyl))bis(3-methyl-1-oxobutane-2,1-diyl)dibenzamide
N,N'-(2S,2'S)-1,1'-(pentane-1,5-diylbis(azanediyl))bis(3-methyl-1-oxobutane-2,1-diyl)dibenzamide
N,N'-(2S,2'S)-1,1'-(octane-1,8-diylbis(azanediyl))bis(3-methyl-1-oxobutane-2,1-diyl)dibenzamide
N,N'-(2S,2'S)-1,1'-(heptane-1,7-diylbis(azanediyl))bis(3-methyl-1-oxobutane-2,1-diyl)dibenzamide
-(2S,2'S)-1,1'-(decane-1,10-diylbis(azanediyl))bis(3-methyl-1-oxobutane-2,1-diyl)dibenzamide
N,N'-(2S,2'S)-1,1'-(nonane-1,9-diylbis(azanediyl))bis(3-methyl-1-oxobutane-2,1-diyl)dibenzamide
N,N'-(2S,2'S)-1,1'-(dodecane-1,12-diylbis(azanediyl))bis(3-methyl-1-oxobutane-2,1-diyl)dibenzamide
N,N'-(2S,2'S)-1,1'-(undecane-1,11-diylbis(azanediyl))bis(3-methyl-1-oxobutane-2,1-diyl)dibenzamide
N,N'-(2S,2'S)-1,1'-(hexadecane-1,16-diylbis(azanediyl))bis(3-methyl-1-oxobutane-2,1-diyl)dibenzamide
N,N'-(2S,2'S)-1,1'-(tridecane-1,13-diylbis(azanediyl))bis(3-methyl-1-oxobutane-2,1-diyl)dibenzamide
N,N'-(2S,2'S)-1,1'-(tetradecane-1,14-diylbis(azanediyl))bis(3-methyl-1-oxobutane-2,1-diyl)dibenzamide
N,N'-(2S,2'S)-1,1'-(octadecane-1,18-diylbis(azanediyl))bis(3-methyl-1-oxobutane-2,1-diyl)dibenzamide

TABLE 2-continued

Non-limiting examples of di-amido gellants of the invention:

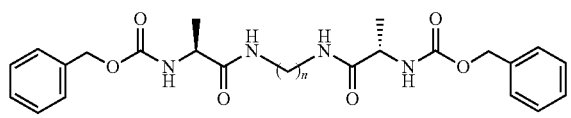

dibenzyl (2S,2'S)-1,1'-(ethane-1,2-diylbis(azanediyl))bis(1-oxopropane-2,1-diyl)dicarbamate
dibenzyl (2S,2'S)-1,1'-(propane-1,3-diylbis(azanediyl))bis(1-oxopropane-2,1-diyl)dicarbamate
dibenzyl (2S,2'S)-1,1'-(butane-1,4-diylbis(azanediyl))bis(1-oxopropane-2,1-diyl)dicarbamate
dibenzyl (2S,2'S)-1,1'-(pentane-1,5-diylbis(azanediyl))bis(1-oxopropane-2,1-diyl)dicarbamate
dibenzyl (2S,2'S)-1,1'-(hexane-1,6-diylbis(azanediyl))bis(1-oxopropane-2,1-diyl)dicarbamate
dibenzyl (2S,2'S)-1,1'-(heptane-1,7-diylbis(azanediyl))bis(1-oxopropane-2,1-diyl)dicarbamate
dibenzyl (2S,2'S)-1,1'-(octane-1,8-diylbis(azanediyl))bis(1-oxopropane-2,1-diyl)dicarbamate
dibenzyl (2S,2'S)-1,1'-(nonane-1,9-diylbis(azanediyl))bis(1-oxopropane-2,1-diyl)dicarbamate
dibenzyl (2S,2'S)-1,1'-(decane-1,10-diylbis(azanediyl))bis(1-oxopropane-2,1-diyl)dicarbamate
dibenzyl (2S,2'S)-1,1'-(undecane-1,11-diylbis(azanediyl))bis(1-oxopropane-2,1-diyl)dicarbamate
dibenzyl (2S,2'S)-1,1'-(dodecane-1,12-diylbis(azanediyl))bis(1-oxopropane-2,1-diyl)dicarbamate
dibenzyl (2S,2'S)-1,1'-(tridecane-1,13-diylbis(azanediyl))bis(1-oxopropane-2,1-diyl)dicarbamate
dibenzyl (2S,2'S)-1,1'-(hexadecane-1,16-diylbis(azanediyl))bis(1-oxopropane-2,1-diyl)dicarbamate
dibenzyl (2S,2'S)-1,1'-(octadecane-1,18-diylbis(azanediyl))bis(1-oxopropane-2,1-diyl)dicarbamate
dibenzyl (2S,2'S)-1,1'-(tetradecane-1,14-diylbis(azanediyl))bis(1-oxopropane-2,1-diyl)dicarbamate

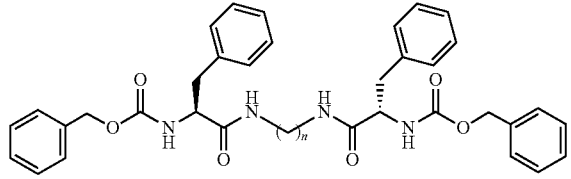

dibenzyl (2S,2'S)-1,1'-(propane-1,3-diylbis(azanediyl))bis(1-oxo-3-phenylpropane-2,1-diyl)dicarbamate
dibenzyl (2S,2'S)-1,1'-(ethane-1,2-diylbis(azanediyl))bis(1-oxo-3-phenylpropane-2,1-diyl)dicarbamate
dibenzyl (2S,2'S)-1,1'-(pentane-1,5-diylbis(azanediyl))bis(1-oxo-3-phenylpropane-2,1-diyl)dicarbamate
dibenzyl (2S,2'S)-1,1'-(butane-1,4-diylbis(azanediyl))bis(1-oxo-3-phenylpropane-2,1-diyl)dicarbamate
dibenzyl (2S,2'S)-1,1'-(heptane-1,7-diylbis(azanediyl))bis(1-oxo-3-phenylpropane-2,1-diyl)dicarbamate
dibenzyl (2S,2'S)-1,1'-(hexane-1,6-diylbis(azanediyl))bis(1-oxo-3-phenylpropane-2,1-diyl)dicarbamate
dibenzyl (2S,2'S)-1,1'-(decane-1,10-diylbis(azanediyl))bis(1-oxo-3-phenylpropane-2,1-diyl)dicarbamate
dibenzyl (2S,2'S)-1,1'-(nonane-1,9-diylbis(azanediyl))bis(1-oxo-3-phenylpropane-2,1-diyl)dicarbamate
dibenzyl (2S,2'S)-1,1'-(dodecane-1,12-diylbis(azanediyl))bis(1-oxo-3-phenylpropane-2,1-diyl)dicarbamate
dibenzyl (2S,2'S)-1,1'-(undecane-1,11-diylbis(azanediyl))bis(1-oxo-3-phenylpropane-2,1-diyl)dicarbamate
dibenzyl (2S,2'S)-1,1'-(hexadecane-1,16-diylbis(azanediyl))bis(1-oxo-3-phenylpropane-2,1-diyl)dicarbamate
dibenzyl (2S,2'S)-1,1'-(tridecane-1,13-diylbis(azanediyl))bis(1-oxo-3-phenylpropane-2,1-diyl)dicarbamate
dibenzyl (2S,2'S)-1,1'-(tetradecane-1,14-diylbis(azanediyl))bis(1-oxo-3-phenylpropane-2,1-diyl)dicarbamate
dibenzyl (2S,2'S)-1,1'-(octadecane-1,18-diylbis(azanediyl))bis(1-oxo-3-phenylpropane-2,1-diyl)dicarbamate

TABLE 2-continued

Non-limiting examples of di-amido gellants of the invention:

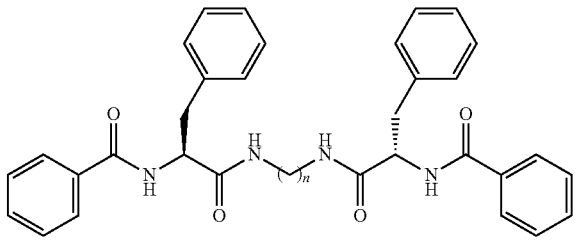

N-N'-(2S,2'S)-1,1'-(decane-1,10-diylbis(azanediyl))bis(1-oxo-3-phenylpropane-2,1-diyl)dibenzamide
N-N'-(2S,2'S)-1,1'-(nonane-1,9-diylbis(azanediyl))bis(1-oxo-3-phenylpropane-2,1-diyl)dibenzamide
N-N'-(2S,2'S)-1,1'-(dodecane-1,12-diylbis(azanediyl))bis(1-oxo-3-phenylpropane-2,1-diyl)dibenzamide
N-N'-(2S,2'S)-1,1'-(undecane-1,11-diylbis(azanediyl))bis(1-oxo-3-phenylpropane-2,1-diyl)dibenzamide
N-N'-(2S,2'S)-1,1'-(hexadecane-1,16-diylbis(azanediyl))bis(1-oxo-3-phenylpropane-2,1-diyl)dibenzamide
N-N'-(2S,2'S)-1,1'-(tridecane-1,13-diylbis(azanediyl))bis(1-oxo-3-phenylpropane-2,1-diyl)dibenzamide
N-N'-(2S,2'S)-1,1'-(tetradecane-1,14-diylbis(azanediyl))bis(1-oxo-3-phenylpropane-2,1-diyl)dibenzamide
N-N'-(2S,2'S)-1,1'-(octadecane-1,18-diylbis(azanediyl))bis(1-oxo-3-phenylpropane-2,1-diyl)dibenzamide

TABLE 3

Non-limiting examples of preferred di-amido gellants of the invention:

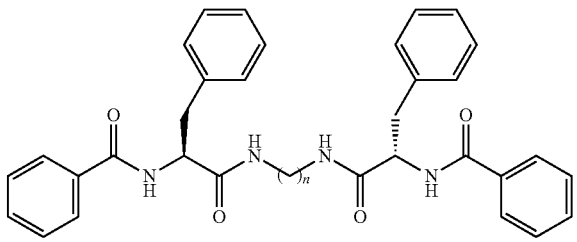

N-N'-(2S,2'S)-1,1'-(ethane-1,2-diylbis(azanediyl))bis(1-oxo-3-phenylpropane-2,1-diyl)dibenzamide
N-N'-(2S,2'S)-1,1'-(propane-1,3-diylbis(azanediyl))bis(1-oxo-3-phenylpropane-2,1-diyl)dibenzamide
N-N'-(2S,2'S)-1,1'-(butane-1,4-diylbis(azanediyl))bis(1-oxo-3-phenylpropane-2,1-diyl)dibenzamide
N-N'-(2S,2'S)-1,1'-(pentane-1,5-diylbis(azanediyl))bis(1-oxo-3-phenylpropane-2,1-diyl)dibenzamide
N-N'-(2S,2'S)-1,1'-(hexane-1,6-diylbis(azanediyl))bis(1-oxo-3-phenylpropane-2,1-diyl)dibenzamide
N-N'-(2S,2'S)-1,1'-(heptane-1,7-diylbis(azanediyl))bis(1-oxo-3-phenylpropane-2,1-diyl)dibenzamide
N-N'-(2S,2'S)-1,1'-(octane-1,8-diylbis(azanediyl))bis(1-oxo-3-phenylpropane-2,1-diyl)dibenzamide

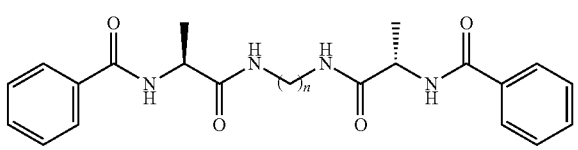

N,N'-(2S,2'S)-1,1'-(propane-1,3-diylbis(azanediyl))bis(1-oxopropane-2,1-diyl)dibenzamide
N,N'-(2S,2'S)-1,1'-(ethane-1,2-diylbis(azanediyl))bis(1-oxopropane-2,1-diyl)dibenzamide
N,N'-(2S,2'S)-1,1'-(pentane-1,5-diylbis(azanediyl))bis(1-oxopropane-2,1-diyl)dibenzamide
N,N'-(2S,2'S)-1,1'-(butane-1,4-diylbis(azanediyl))bis(1-oxopropane-2,1-diyl)dibenzamide

TABLE 3-continued

Non-limiting examples of preferred di-amido gellants of the invention:

N,N'-(2S,2'S)-1,1'-(heptane-1,7-diylbis(azanediyl))bis(1-oxopropane-2,1-diyl)dibenzamide
N,N'-(2S,2'S)-1,1'-(hexane-1,6-diylbis(azanediyl))bis(1-oxopropane-2,1-diyl)dibenzamide
N,N'-(2S,2'S)-1,1'-(nonane-1,9-diylbis(azanediyl))bis(1-oxopropane-2,1-diyl)dibenzamide
N,N'-(2S,2'S)-1,1'-(octane-1,8-diylbis(azanediyl))bis(1-oxopropane-2,1-diyl)dibenzamide
N,N'-(2S,2'S)-1,1'-(undecane-1,11-diylbis(azanediyl))bis(1-oxopropane-2,1-diyl)dibenzamide
N,N'-(2S,2'S)-1,1'-(decane-1,10-diylbis(azanediyl))bis(1-oxopropane-2,1-diyl)dibenzamide
N,N'-(2S,2'S)-1,1'-(tridecane-1,13-diylbis(azanediyl))bis(1-oxopropane-2,1-diyl)dibenzamide
N,N'-(2S,2'S)-1,1'-(dodecane-1,12-diylbis(azanediyl))bis(1-oxopropane-2,1-diyl)dibenzamide
N,N'-(2S,2'S)-1,1'-(octadecane-1,18-diylbis(azanediyl))bis(1-oxopropane-2,1-diyl)dibenzamide
N,N'-(2S,2'S)-1,1'-(hexadecane-1,16-diylbis(azanediyl))bis(1-oxopropane-2,1-diyl)dibenzamide
dibenzyl (2S-2'S)-1,1'-(octane-1,8-diylbis(azanediyl))bis(1-oxo-3-phenylpropane-2,1-diyl)dicarbamate
N,N'-(2S,2'S)-1,1'-(tetradecane-1,14-diylbis(azanediyl))bis(1-oxopropane-2,1-diyl)dibenzamide

TABLE 4

Non-limiting examples of other preferred di-amido gellants of the invention:

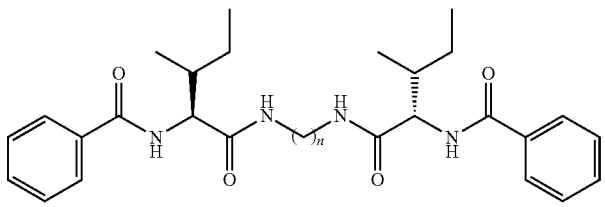

{1-[2-(2-Benzyloxycarbonylamino-3-methyl-pentanoylamino)-ethylcarbamoyl]-2-methyl-butyl}-carbamic acid benzyl ester
{1-[3-(2-Benzyloxycarbonylamino-3-methyl-pentanoylamino)-octylcarbamoyl]-2-methyl-butyl}-carbamic acid benzyl ester
{1-[4-(2-Benzyloxycarbonylamino-3-methyl-pentanoylamino)-butylcarbamoyl]-2-methyl-butyl}-carbamic acid benzyl ester
{1-[5-(2-Benzyloxycarbonylamino-3-methyl-pentanoylamino)-pentylcarbamoyl]-2-methyl-butyl}-carbamic acid benzyl ester
{1-[6-(2-Benzyloxycarbonylamino-3-methyl-pentanoylamino)-hexylcarbamoyl]-2-methyl-butyl}-carbamic acid benzyl ester
{1-[7-(2-Benzyloxycarbonylamino-3-methyl-pentanoylamino)-heptylcarbamoyl]-2-methyl-butyl}-carbamic acid benzyl ester
{1-[8-(2-Benzyloxycarbonylamino-3-methyl-pentanoylamino)-octylcarbamoyl]-2-methyl-butyl}-carbamic acid benzyl ester
{1-[9-(2-Benzyloxycarbonylamino-3-methyl-pentanoylamino)-nonylcarbamoyl]-2-methyl-butyl}-carbamic acid benzyl ester
{1-[10-(2-Benzyloxycarbonylamino-3-methyl-pentanoylamino)-decylcarbamoyl]-2-methyl-butyl}-carbamic acid benzyl ester
{1-[711(2-Benzyloxycarbonylamino-3-methyl-pentanoylamino)-undecylcarbamoyl]-2-methyl-butyl}-carbamic acid benzyl ester
{1-[12-(2-Benzyloxycarbonylamino-3-methyl-pentanoylamino)-dodecylcarbamoyl]-2-methyl-butyl}-carbamic acid benzyl ester

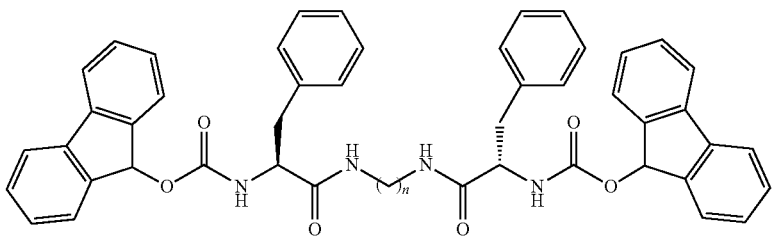

(1-Benzyl-2-{2-[2-(9H-fluoren-9-yloxycarbonylamino)-3-phenyl-propionylamino]-ethylamino}-ethyl)-carbamic acid 9H-fluoren-9-yl ester
(1-Benzyl-2-{3-[2-(9H-fluoren-9-yloxycarbonylamino)-3-phenyl-propionylamino]-propylamino}-ethyl)-carbamic acid 9H-fluoren-9-yl ester
(1-Benzyl-2-{4-[2-(9H-fluoren-9-yloxycarbonylamino)-3-phenyl-propionylamino]-butylamino}-ethyl)-carbamic acid 9H-fluoren-9-yl ester
(1-Benzyl-2-{5-[2-(9H-fluoren-9-yloxycarbonylamino)-3-phenyl-propionylamino]-pentylamino}-ethyl)-carbamic acid 9H-fluoren-9-yl ester
(1-Benzyl-2-{6-[2-(9H-fluoren-9-yloxycarbonylamino)-3-phenyl-propionylamino]-hexylamino}-ethyl)-carbamic acid 9H-fluoren-9-yl ester TABLE 4-continued Non-limiting examples of other preferred di-amido gellants of the invention:

(1-Benzyl-2-{7-[2-(9H-fluoren-9-yloxycarbonylamino)-3-phenyl-propionylamino]-heptylamino}-
ethyl)-carbamic acid 9H-fluoren-9-yl ester
(1-Benzyl-2-{8-[2-(9H-fluoren-9-yloxycarbonylamino)-3-phenyl-propionylamino]-octylamino}-
ethyl)-carbamic acid 9H-fluoren-9-yl ester
(1-Benzyl-2-{9-[2-(9H-fluoren-9-yloxycarbonylamino)-3-phenyl-propionylamino]-nonylamino}-
ethyl)-carbamic acid 9H-fluoren-9-yl ester
(1-Benzyl-2-{10-[2-(9H-fluoren-9-yloxycarbonylamino)-3-phenyl-propionylamino]-decylamino}-
ethyl)-carbamic acid 9H-fluoren-9-yl ester
(1-Benzyl-2-{11-[2-(9H-fluoren-9-yloxycarbonylamino)-3-phenyl-propionylamino]-undecylamino}-
ethyl)-carbamic acid 9H-fluoren-9-yl ester
(1-Benzyl-2-{12-[2-(9H-fluoren-9-yloxycarbonylamino)-3-phenyl-propionylamino]-dodecylamino}-
ethyl)-carbamic acid 9H-fluoren-9-yl ester

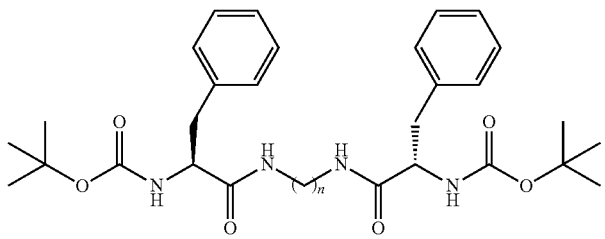

tert-butyl N-[(1S)-1-benzyl-2-[2-[[(2S)-2-(tert-butoxycarbonylamino)-3-phenyl-
propanoyl]amino]ethylamino]-2-oxo-ethyl]carbamate
tert-butyl N-[(1S)-1-benzyl-2-[3-[[(2S)-2-(tert-butoxycarbonylamino)-3-phenyl-
propanoyl]amino]propylamino]-2-oxo-ethyl]carbamate
tert-butyl N-[(1S)-1-benzyl-2-[4-[[(2S)-2-(tert-butoxycarbonylamino)-3-phenyl-
propanoyl]amino]butylamino]-2-oxo-ethyl]carbamate
tert-butyl N-[(1S)-1-benzyl-2-[5-[[(2S)-2-(tert-butoxycarbonylamino)-3-phenyl-
propanoyl]amino]pentylamino]-2-oxo-ethyl]carbamate
tert-butyl N-[(1S)-1-benzyl-2-[6-[[(2S)-2-(tert-butoxycarbonylamino)-3-phenyl-
propanoyl]amino]hexylamino]-2-oxo-ethyl]carbamate
tert-butyl N-[(1S)-1-benzyl-2-[7-[[(2S)-2-(tert-butoxycarbonylamino)-3-phenyl-
propanoyl]amino]heptylamino]-2-oxo-ethyl]carbamate
tert-butyl N-[(1S)-1-benzyl-2-[8-[[(2S)-2-(tert-butoxycarbonylamino)-3-phenyl-
propanoyl]amino]octylamino]-2-oxo-ethyl]carbamate
tert-butyl N-[(1S)-1-benzyl-2-[9-[[(2S)-2-(tert-butoxycarbonylamino)-3-phenyl-
propanoyl]amino]nonylamino]-2-oxo-ethyl]carbamate
tert-butyl N-[(1S)-1-benzyl-2-[10-[[(2S)-2-(tert-butoxycarbonylamino)-3-phenyl-
propanoyl]amino]decylamino]-2-oxo-ethyl]carbamate
tert-butyl N-[(1S)-1-benzyl-2-[11-[[(2S)-2-(tert-butoxycarbonylamino)-3-phenyl-
propanoyl]amino]undecylamino]-2-oxo-ethyl]carbamate
tert-butyl N-[(1S)-1-benzyl-2-[12-[[(2S)-2-(tert-butoxycarbonylamino)-3-phenyl-
propanoyl]amino]dodecylamino]-2-oxo-ethyl]carbamate Water and/or Non-Aminofunctional Organic Solvent:

The consumer product composition may be dilute or concentrated aqueous liquids. Alternatively, the consumer product composition may be almost entirely non-aqueous, and comprise a non-aminofunctional organic solvent. Such consumer product compositions may contain very little water, for instance, that may be introduced with other raw materials. Preferably, the consumer product composition comprises from 1% to 95% by weight of water and/or non-aminofunctional organic solvent. For concentrated detergents, the composition comprises preferably from 5% to 70%, more preferably from 10% to 50%, most preferably from 15% to 45% by weight, water and/or non-aminofunctional organic solvent.

As used herein, "non-aminofunctional organic solvent" refers to any organic solvent which contains no amino functional groups. Preferred non-aminofunctional organic solvents include monohydric alcohols, dihydric alcohols, polyhydric alcohols, glycerol, glycols, polyalkylene glycols such as polyethylene glycol, and mixtures thereof. Highly preferred are mixtures of solvents, especially mixtures of two or more of the following: lower aliphatic alcohols such as ethanol, propanol, butanol, isopropanol; diols such as 1,2-propanediol or 1,3-propanediol; and glycerol. Also preferred are propanediol and mixtures thereof with diethylene glycol where the mixture contains no methanol or ethanol. Thus consumer product compositions may include embodiments in which propanediols are used but methanol and ethanol are not used.

Preferable non-aminofunctional organic solvents are liquid at ambient temperature and pressure (i.e. 21° C. and 1 atmosphere), and comprise carbon, hydrogen and oxygen. Non-aminofunctional organic solvents may be present when preparing a premix of the external structuring system, or in the final consumer product composition.

Method of Making Di-Amido Gellants:

Materials can be bought from Iris Biotech GmbH, Waldershofer Str. 49-51, 95615 Marktredwitz, Germany; Bachem

Example Method 1

Synthesis of dibenzyl (2S,2'S)-1,1'-(propane-1,3-diylbis(azanediyl))bis(3-methyl-1-oxobutane-2,1-diyl)dicarbamate

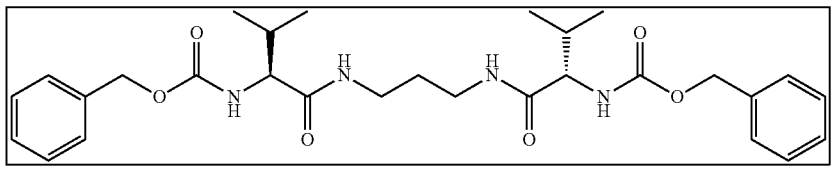

A first solution is prepared by dissolving N-alpha-Benzyloxycarbonyl-L-valine (17.60 grams, 70 mmol) and N-hydroxysuccinimide (8.79 g, 77 mmol) in dry THF at 0° C. Once a clear solution is obtained, 17.45 grams of N,N'-Dicyclohhexylcarbodiimide (84.6 mmol) in anhydrous THF is slowly added to the first solution and the resulting mixture is stirred at 0-5° C. in ice-bath for 24 h. The intermediate formed (white solid, 90% yield) is filtered off (filtering plate no 3) and the filtrate was concentrated to dryness. The crude product was recrystallized from 2-propanol to furnish the pure product.

Then, dibenzyl (2S,2'S)-1,1'-(propane-1,3-diylbis(azanediyl))bis(3-methyl-1-oxobutane-2,1-diyl)dicarbamate is obtained by preparing a second solution by dissolving 11.74 grams intermediate formed (33.7 mmol) in 150 ML anhydrous dimethyl ether and cooled in an ice bath. 1.11 grams 1,3-Diaminopropane (15.0 mmol) dissolved in 20 mL dry dimethyl ether is slowly added. The reaction mixture is stirred at 20 C for 18 hours and then is warmed for 6 hours at 45 C. The dibenzyl (2S,2'S)-1,1'-(propane-1,3-diylbis(azanediyl))bis(3-methyl-1-oxobutane-2,1-diyl)dicarbamate is filtered as a white solid and washed with cold water and cold methanol. The yield obtained is 85%.

Example Method 2

{1-[7-(2-Benzyloxycarbonylamino-3-methyl-pentanoylamino)-heptylcarbamoyl]-2-methyl-butyl}-carbamic acid benzyl ester

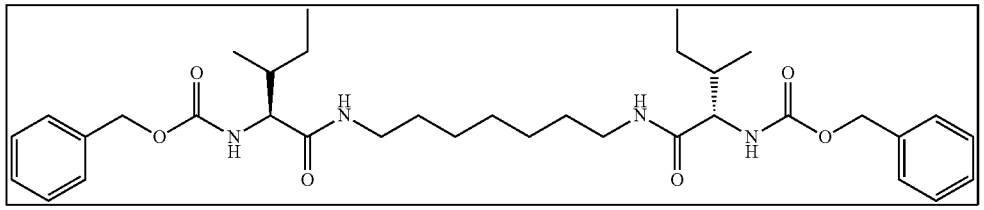

A first solution is prepared by dissolving N-alpha-Benzyloxycarbonyl-L-isoleucine (18.57 grams, 70 mmol) and N-hydroxysuccinimide (8.79 g, 77 mmol) in dry THF at 0° C. Once a clear solution is obtained, 17.45 grams of N,N'-Dicyclohhexylcarbodiimide (84.6 mmol) in anhydrous THF is slowly added to the first solution and the resulting mixture is stirred at 0-5° C. in ice-bath for 24 h. The intermediate formed (white solid, 84% yield) is filtered off (filtering plate no 3) and the filtrate was concentrated to dryness. The crude product was recrystallized from 2-propanol to furnish the pure product.

Then, {1-[7-(2-Benzyloxycarbonylamino-3-methyl-pentanoylamino)-heptylcarbamoyl]-2-methyl-butyl}-carbamic acid benzyl ester is obtained by preparing a second solution by dissolving 11.74 grams intermediate formed (33.7 mmol) in 150 ML anhydrous dimethyl ether and cooled in an ice bath. 1.95 grams 1,7-diaminoheptane (15.0 mmol) dissolved in 20 mL dry dimethyl ether is slowly added. The reaction mixture is stirred at 20 C for 18 hours and then is warmed for 6 hours at 45 C. The {1-[7-(2-Benzyloxycarbonylamino-3-methyl-pentanoylamino)-heptylcarbamoyl]-2-methyl-butyl}-carbamic acid benzyl ester is filtered as a white solid and washed with cold water and cold methanol. The yield obtained is 69%. {1-[7-(2-Benzyloxycarbonylamino-3-methyl-pentanoylamino)-heptylcarbamoyl]-2-methyl-butyl}-carbamic acid benzyl ester is characterized:

IR (KBr): 3299, 3094, 3067, 3033, 2963, 2929, 2875, 2856, 1690, 1645, 1538 cm$^{-1}$.

$^1$H NMR (300 MHz, [D6]DMSO, 30° C.): δ=0.78 (dd, J=6.8, 4.4 Hz, 6H), 1.08 (m, 1H), 1.21 (s, 3H), 1.38 (m, 2H), 1.67 (d, J=5.2 Hz, 1H), 2.94 (m, 1H), 3.08 (dd, J=12.9, 6.2 Hz, 1H), 3.80 (t, J=8.3 Hz, 1H), 5.00 (s, 2H), 7.17 (d, J=8.8 Hz, 1H), 7.34 (m, 5H), 7.84 (m, 1H) ppm.

$^{13}$CNMR (126 MHz, [D6]DMSO, 30° C.): δ=171.35, 156.39, 137.56, 128.72, 128.15, 128.03, 65.75, 59.67, 38.81, 36.82, 29.35, 28.83, 26.76, 24.86, 15.82, 11.34.

HRMS (ESI-TOF+): calcd. for $C_{35}H_{52}N_4O_6Na^+$[M+Na]$^+$=647.3785; found=647.3787 (Δ=0.3 ppm).

Test Methods:

1. Turbidity (NTU):

The turbidity (measured in NTU: Nephelometric Turbidity Units) is measured using a Hach 2100P turbidity meter calibrated according to the procedure provided by the manufacture. The sample vials are filled with 15 ml of representative sample and capped and cleaned according to the operating instructions. If necessary, the samples are degassed to remove any bubbles either by applying a vacuum or using an ultrasonic bath (see operating manual for procedure). The turbidity is measured using the automatic range selection.

2. Minimum Gelling Concentration (MGC)

MGC is calculated by a tube inversion method based on R. G. Weiss, P. Terech; "Molecular Gels: Materials with self-assembled fibrillar structures" 2006 springer, p 243. In order to determine the MGC, three screenings are done:
  a) First screening: prepare several vials increasing the di-amido gellant concentration from 0.5% to 5.0 weight % in 0.5% steps
  b) Determine in which interval the gel is formed (one inverted sample still flowing and the next one is already a strong gel). In case no gel is formed at 5%, higher concentrations are used.
  c) Second screening: prepare several vials increasing the di-amido gellant concentration in 0.1 weight % steps in the interval determined in the first screening.
  d) Determine in which interval the gel is formed (one inverted sample still flowing and the next one is already a strong gel)
  e) Third screening: in order to have a very precise percentage of the MGC, run a third screening in 0.025 weight % steps in the interval determined in the second screening.
  f) The Minimum Gelling Concentration (MGC) is the lowest concentration which forms a gel in the third screening (does not flow on inversion of the sample).

For each screening, samples are prepared and treated as follows: 8 mL vials (Borosilacate glass with Teflon cap, ref. B7857D, Fisher Scientific Bioblock) are filled with 2.0000±0.0005 g (KERN ALJ 120-4 analytical balance with ±0.1 mg precision) of the fluid (comprising the consumer product composition and di-amido gellant) for which we want to determine the MGC. The vial is sealed with the screw cap and left for 10 minutes in an ultrasound bath (Elma Transsonic T 710 DH, 40 kHz, 9.5 L, at 25° C. and operating at 100% power) in order to disperse the solid in the liquid. Complete dissolution is then achieved by heating, using a heating gun (Bosch PHG-2), and gentle mechanical stirring of the vials. It is crucial to observe a completely clear solution. Handle vials with care. While they are manufactured to resist high temperatures, a high solvent pressure may cause the vials to explode. Vials are cooled to 25° C., for 10 min in a thermostatic bath (Compatible Control Thermostats with controller CC2, D77656, Huber). Vials are inverted, left inverted for 1 minute, and then observed for which samples do not flow. After the third screening, the concentration of the sample that does not flow after this time is the MGC. For those skilled in the art, it is obvious that during heating solvent vapours may be formed, and upon cooling down the samples, these vapours can condense on top of the gel. When the vial is inverted, this condensed vapour will flow. This is discounted during the observation period. If no gels are obtained in the concentration interval, higher concentrations must be evaluated.

3. Rheology

An AR-G2 rheometer from TA Instruments is used for rheological measurements. Plate: 40 mm standard steel parallel plate, 300 µm gap.

1. Gel strength: The gel strength is measured using a stress sweep test whereby the oscillation stress is increased from 0.001 Pa to 10 Pa, taking 10 points per decade at 20° C. and at a frequency of 1 Hz. We use G' and G" within the linear viscoelastic region and the oscillation stress at the point where G' and G" cross over as a measure for the gel strength, as shown in FIG. 1.

Figure 2:
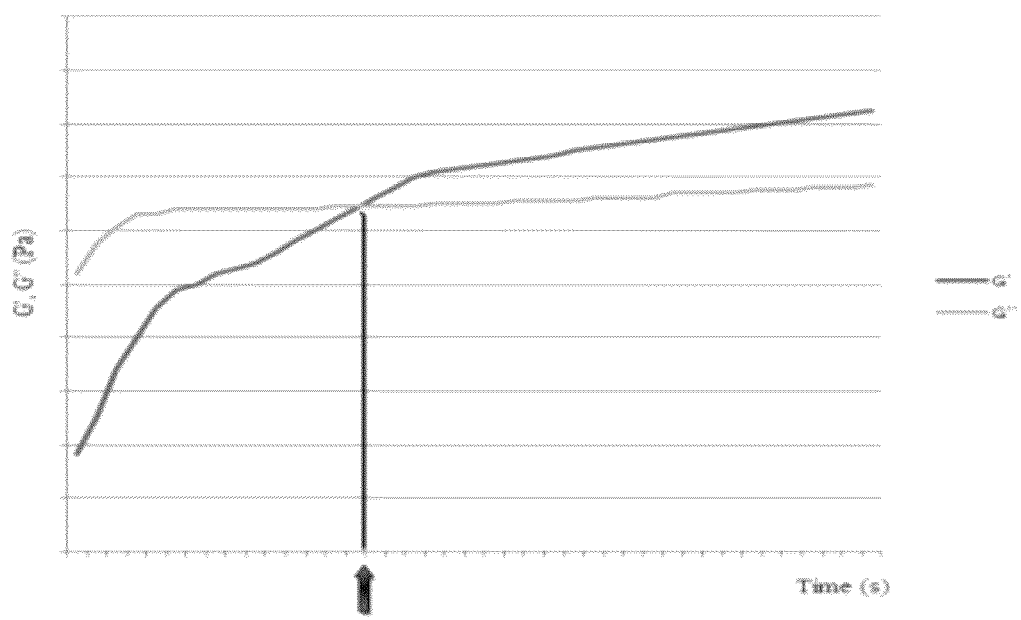
FIG. 2 details G' and G" cross over as a measure of restructuring kinetics.

2. Recovery of structure: first we apply a pre-shear of 30 s-1 at 20° C. for 60 s, after which we follow how the structure recovers applying a time sweep test with an oscillation stress of 0.02 Pa and a single frequency of 1 Hz at 20° C. for 10 minutes. As a measure of the restructuring kinetics, we use G' and G" cross over, as shown in the FIG. 2.

EXAMPLES

Example 1

A Liquid Laundry Detergent Composition is Prepared as Follows

Step 1: A structurant premix A1 is prepared by dissolving 0.20 g dibenzyl (2S,2'S)-1,1'-(propane-1,3-diylbis(azanediyl))bis(3-methyl-1-oxobutane-2,1-diyl)dicarbamate in 9.8 g solvent (1,2-propanediol).

Step 2: A detergent feed B1 comprising the temperature—insensitive ingredients and having the to composition described in Table 5 is prepared.

TABLE 5

Composition of detergent feed B1

| Ingredient | Detergent Feed B1 Grams |
|---|---|
| Linear Alkylbenzene sulfonic acid (LAS) | 12.0 |
| C12-14 alkyl ethoxy 3 sulfate Mono Ethanol Amine salt | 9.3 |
| C12-14 alkyl 7-ethoxylate | 8.0 |
| Citric acid | 3.0 |
| C12-18 Fatty Acid | 10.0 |
| Grease Cleaning Alkoxylated Polyalkylenimine Polymer[1] | 0.9 |
| PEG PVAc Polymer[2] | 0.9 |
| Soil Suspending Alkoxylated Polyalkylenimine Polymer[3] | 2.2 |
| Hydroxyethane diphosphonic acid | 1.6 |
| FWA | 0.23 |
| Ethanol | 1.5 |
| Boric acid | 0.5 |
| MEA | Up to pH 8 |
| Water up to | 66 grams |

[1]600 g/mol molecular weight polyethylenimine core with 24 ethoxylate groups per —NH and 16 propoxylate groups per —NH.
[2]PEG-PVA graft copolymer is a polyvinyl acetate grafted polyethylene oxide copolymer having a polyethylene oxide backbone and multiple polyvinyl acetate side chains. The molecular weight of the polyethylene oxide backbone is 6000 and the weight ratio of the polyethylene oxide to polyvinyl acetate is 40 to 60 and no more than 1 grafting point per 50 ethylene oxide units.
[3]600 g/mol molecular weight polyethylenimine core with 20 ethoxylate groups per —NH.

Step 3: 10 grams of structurant premix A1 heated up to 100° C. is mixed with 66 grams of detergent feed B1 heated up to 60° C. at 400 rpm for 2 min, and the resulting mixture is let to cool down.

Step 4: When the temperature has dropped below 45° C., the heat—sensitive ingredients (1.5 gram protease, 0.7 gram amylase, 0.1 gram mannanase, 0.1 gram xyloglucanase, 0.4 gram pectate lyase and 1.7 gram of perfume) and 19.5 grams of deionized water are added under gentle stirring, at 300-400 rpm for 5 min, and the detergent composition is left to cool down to room temperature without any further agitation.

TABLE 6

Rheology Data

| | Gel strength | | | |
|---|---|---|---|---|
| Example n. | G' (Pa) | G" (Pa) | Oscillation stress (Pa) | Recovery Time (s) |
| 1 | 8.2 | 7.6 | 0.04 | 400 |

Example 2

Unit Dose Laundry Detergent

A liquid laundry detergent composition is prepared as follows:

Step 1: A structurant premix A2 is prepared by adding 0.53 g dibenzyl (2S,2'S)-1,1'-(propane-1,3-diylbis(azanediyl))bis(3-methyl-1-oxobutane-2,1-diyl)dicarbamate in 39.47 grams of 1,2 propanediol and heating the mixture under stirring to 110° C. until fully dissolved.

Step 2: A detergent feed B2 having the composition described in Table 7 is prepared.

TABLE 7

Composition of detergent feed B2

| Ingredient | Detergent Feed B2 % of base @100% active |
|---|---|
| 1,2-Propanediol | 10 |
| Citric Acid | 0.5 |
| MEA | 10 |
| Glycerol | 5 |
| Hydroxyethane diphosphonic acid | 1 |
| Potassium sulfite | 0.2 |
| C12-45 alkyl 7-ethoxylate | 20 |
| Linear Alkylbenzene sulfonic acid | 24.5 |
| FWA | 0.2 |
| C12-18 Fatty Acid | 16 |
| Ethoxysulfated Hexamethylene Diamine Dimethyl Quat | 2.9 |
| Soil Suspending Alkoxylated Polyalkylenimine Polymer[3] | 1 |
| MgCl$_2$ | 0.2 |
| Protease enzyme | 1.4 |
| Mannanase enzyme | 0.1 |
| Amylase enzyme | 0.2 |
| Water & minors | Up to 100% |

Step 3: 3 grams of structurant premix A2 are heated to 100° C. while detergent feed B2 is heated to 60° C. The 3 grams of structurant premix A2 are added to 37 grams of detergent feed B2.

Step 4: After mixing at 400 rpm for 2 minutes, the resulting mixture is allowed to cool to room temperature to form the consumer product composition.

The consumer product composition is then packed into a polyvinyl alcohol pouch using standard techniques horizontal form fill techniques. The water soluble film material was Monosol M-8630.

Examples 3A to 3D

A Liquid Laundry Detergent Composition is Prepared as Follows

Step 1: The di-amido gellant premix is prepared by adding the required amount of dibenzyl (2S,2'S)-1,1'-(propane-1,3-diylbis(azanediyl))bis(3-methyl-1-oxobutane-2,1-diyl)dicarbamate in the required amount of ethanol and heating the mixture to 77° C. until fully dissolved.

Step 2: A detergent feed is created from the remaining ingredients by the same means as Example 1 Step 2.

Step 3: The required amount of the di-amido gellant premix is heated up to 77° C. and mixed with the required amount of detergent premix at 60° C. (mixing at 400 rpm for 2 min). The resulting mixture is allowed to cool down.

TABLE 8

Fluid laundry detergent composition comprising a di-amido gellant:

| Component | % w/w liquid laundry detergent composition | | | |
|---|---|---|---|---|
| | 3A | 3B | 3C | 3D |
| C11.8 linear alkylbenzene sulfonic acid | 17.2 | 17.2 | 13.5 | 14.0 |
| Neodol 23-5 | | | 5.2 | |
| Neodol 23-9 | 10.4 | 10.4 | 5.2 | 8.4 |
| Citric acid | 5.0 | 5.0 | 4.5 | 4.1 |
| DTPA[1] | 0.3 | 0.3 | 0.2 | 0.2 |
| Ethanolamine | 3.3 | 3.3 | 2.6 | 2.6 |
| Sodium hydroxide | 0.6 | to adjust pH | to adjust pH | to adjust pH |
| ethoxylated amine polymer | 2.0 | 2.0 | 1.6 | 1.6 |
| ethanol[2] | 2.0 | 2.0 | 2.0 | 2.0 |
| silicone suds suppressor | 0.04 | 0.04 | 0.03 | 0.03 |
| Tinopal CBS-X | 0.2 | 0.2 | 0.2 | 0.2 |
| Perfume | 0.3 | 0.3 | 0.2 | 0.2 |
| Blue EM[3] | 0.005 | | | |
| Basic Violet 3 (CI 42555)[4] | | 0.005 | | |
| Basic Violet 4 (CI 42600)[5] | | | 0.001 | |
| Acid Blue 7 (CI 42080)[6] | | 0.0003 | | |
| dibenzyl (2S,2'S)-1,1'-(propane-1,3-diylbis(azanediyl))bis(3-methyl-1-oxobutane-2,1-diyl)dicarbamate[7] | 0.125 | 0.250 | 0.250 | 0.250 |
| water | balance | balance | balance | balance |
| neat pH (of composition) | 3.2 | 3.2 | 2.5 | 2.7 |
| reserve acidity[8] | 2.5 | 2.5 | 2.9 | 2.5 |
| Misc Balance Water | 0.1 | 0.1 | 0.1 | 0.1 |

[1] diethyleneetriaminepentaacetic acid sodium salt
[2] added via di-amido gellant premix
[3] polymeric colorant supplied by Milliken
[4,5] fabric hueing dyes
[6] non-fabric substantive dye
[7] added via di-amido gellant premix
[8] gNaOH/100 g of product

Examples 4A to 4E

Fluid Detergent Fabric Care Compositions Comprising Amido-Gellants of the Present Invention Fluid detergent fabric care compositions may be prepared by mixing together the ingredients listed in the proportions shown:

TABLE 9

Fluid Detergent Fabric Care Compositions comprising amido-gellants:

| Ingredient | 4A Wt % | 4B Wt % | 4C Wt % | 4D Wt % | 4E Wt % |
|---|---|---|---|---|---|
| C12-15 alkyl polyethoxylate (3.0) sulfate | 3.8 | 3.8 | 3.8 | 2.8 | 3.3 |
| C11.8 linear alkylbenzene sulfonc acid | 11 | 11 | 9.3 | 6.4 | 9.5 |
| C14-15 alkyl 7-ethoxylate | 6.7 | 6.7 | 1.9 | 2.1 | 9.5 |
| C12-14 alkyl 7-ethoxylate | 0.5 | 0.5 | 0.5 | 0.5 | 0.5 |
| 1,2 Propane diol | 4 | 3 | 4 | 4 | 4 |
| Ethanol | 1 | 1 | 1 | 1 | 1 |
| Di Ethylene Glycol | — | 2 | — | — | — |
| Na Cumene Sulfonate | 3 | 3 | 3 | 3 | 3 |

TABLE 9-continued

Fluid Detergent Fabric Care Compositions comprising amido-gellants:

| Ingredient | 4A Wt % | 4B Wt % | 4C Wt % | 4D Wt % | 4E Wt % |
|---|---|---|---|---|---|
| $C_{12-18}$ Fatty Acid | 2.6 | 2.6 | 3.3 | 2.6 | 2.6 |
| Citric acid | 2.6 | 2.6 | 3.7 | 4.3 | 2.6 |
| Protease (40.6 mg/g/)[1] | 0.5 | 0.5 | 0.5 | 0.5 | 0.5 |
| Natalase 200L (29.26 mg/g)[2] | 0.1 | 0.1 | 0.1 | 0.1 | 0.1 |
| Termamyl Ultra (25.1 mg/g)[2] | 0.05 | 0.05 | 0.05 | 0.05 | 0.05 |
| Mannaway 25L (25 mg/g)[2] | 0.05 | 0.05 | 0.05 | 0.05 | 0.05 |
| Lipase (16.91 mg/g)[2] | 0.5 | — | 0.25 | — | 0.5 |
| Lipolex ®[2] | — | 0.2 | — | — | — |
| Lipex ®[2] | — | — | — | 0.25 | — |
| Whitezyme (20 mg/g)[2] | 0.05 | 0.05 | 0.05 | 0.05 | 0.05 |
| Fluorescent Whitening Agent | 0.1 | 0.1 | 0.1 | 0.1 | 0.1 |
| Diethylene Triamine Penta Acetic acid | — | 0.5 | — | — | — |
| Diethylene Triamine Penta Methylene Phosphonic acid | 0.3 | 0.1 | 0.3 | 0.3 | 0.3 |
| Soil Suspending Alkoxylated Polyalkylenimine Polymer[3] | 0.8 | 0.5 | — | — | 0.8 |
| Zwitterionic ethoxylated quaternized sulfated hexamethylene diamine[4] | 1 | 1 | 0.9 | 1 | 1 |
| Grease Cleaning Alkoxylated Polyalkylenimine Polymer[5] | 0.4 | 0.4 | — | 0.2 | — |
| PEG-PVAc Polymer[6] | — | 0.5 | — | — | — |
| Monoethanolamine Borate | 2.0 | 1.0 | 2.0 | 2.0 | 2.0 |
| 4-Formyl Phenyl Boronic Acid | — | 0.03 | — | — | — |
| Sodium formate | 0.4 | 0.4 | 0.4 | 0.4 | 0.4 |
| Calcium chloride | 0.05 | 0.05 | 0.05 | 0.05 | 0.05 |
| dibenzyl (2S,2'S)-1,1'-(propane-1,3-diylbis(azanediyl))bis(3-methyl-1-oxobutane-2,1-diyl)dicarbamate | 0.2 | 0.24 | 0.2 | 0.28 | 0.28 |
| Acticide MBS 2550 | 0.005 | 0.005 | 0.005 | 0.005 | 0.005 |
| Perfume Microcapsules | — | — | — | 0.2 | — |
| Mica | — | — | — | — | 0.05 |
| Silicone suds suppressor | — | 0.1 | — | — | — |
| Water, perfumes, dyes, neutralizers, and other optional components (pH to 8.0-8.2) | to 100% | to 100% | to 100% | to 100% | to 100% |

[1]Available from Genencor International, South San Francisco, CA.
[2]Available from Novozymes, Denmark.
[3]600 g/mol molecular weight polyethylenimine core with 20 ethoxylate groups per —NH. Available from BASF (Ludwigshafen, Germany)
[4]Described in WO 01/05874 and available from BASF (Ludwigshafen, Germany)
[5]600 g/mol molecular weight polyethylenimine core with 24 ethoxylate groups per —NH and 16 propoxylate groups per —NH. Available from BASF (Ludwigshafen, Germany).
[6]PEG-PVA graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units. Available from BASF (Ludwigshafen, Germany).

Examples 5A to 5T

Hand-Dish Washing Fluid Detergent Compositions Comprising Amido-Gellants

Hand-dish washing liquid detergent compositions may be prepared by mixing together the ingredients listed in the proportions shown:

TABLE 10

Hand-dish washing fluid detergent compositions comprising amido-gellants:

| | Ex 5A | Ex 5B | Ex 5C | Ex 5D | Ex 5E | Ex 5F |
|---|---|---|---|---|---|---|
| Alkyl Ethoxy Sulfate AE0.6S | 22.0 | 19.0 | 27.0 | 20.0 | 22.0 | 22.0 |
| Linear C12-C14 Amine oxide | 6.0 | 4.5 | — | — | 6.0 | 5.0 |
| C9-C11 alkyl EO8 ethoxylate | 7.0 | — | — | — | — | — |
| L-Glutamic acid-N,N-di(acetic acid)tetrasodium salt | 1.0 | — | — | 0.1 | — | — |
| Sodium Citrate | — | 1.0 | — | 0.5 | 0.8 | — |
| Solvent: ethanol, isopropylalcohol, . . . | 2.5 | 4.0 | 3.0 | 2.0 | 3.0 | 2.5 |
| Polypropylene glycol MW2000 | 1.0 | 0.5 | 1.0 | — | 2.0 | 1.0 |
| Sodium Chloride | 0.5 | 1.0 | 1.0 | 0.5 | 0.5 | 0.5 |
| dibenzyl (2S,2'S)-1,1'-(propane-1,3-diylbis(azanediyl))bis(3-methyl-1-oxobutane-2,1-diyl)dicarbamate | 0.50 | 0.20 | 0.30 | 0.15 | 0.25 | 0.20 |

Minors and Balance with water up to 100%

TABLE 11

Hand-dish washing fluid detergent compositions comprising amido-gellants:

| | Ex 5G | Ex 5H | Ex 5I | Ex 5J |
|---|---|---|---|---|
| Alkyl Ethoxy Sulfate AE1.0S | 13 | 16 | 17 | 20 |
| C12-C14 Amine oxide | 4.5 | 5.5 | 4.0 | 4.5 |
| C9-C11 alkyl EO8 ethoxylate | 4 | 4 | — | — |
| L-Glutamic acid-N,N-di(acetic acid) tetrasodium salt | 0.7 | — | — | — |
| Sodium Citrate | — | — | 0.2 | — |
| Solvent: ethanol, isopropylalcohol, . . . | 2.0 | 2.0 | 2.0 | 1.5 |
| Polypropylene glycol MW 2000 | 0.5 | 0.3 | 0.5 | 0.8 |
| Sodium Chloride | 0.5 | 0.8 | 0.4 | 0.5 |
| dibenzyl (2S,2'S)-1,1'-(hexane-1,6-diylbis(azanediyl))bis(1-oxo-3-phenylpropane-2,1-diyl)dicarbamate | 0.15 | 0.12 | 0.18 | 0.21 |

Minors and Balance with water up to 100%

TABLE 12

Hand-dish washing fluid detergent compositions comprising amido-gellants:

| | Ex 5K | Ex 5L | Ex 5M | Ex 5N | Ex 5O |
|---|---|---|---|---|---|
| Linear Alkylbenzene Sulfonate | 21.0 | 21.0 | 12.0 | 13.0 | — |
| Alkyl Ethoxy Sulfate AE1.0S | — | — | 14.0 | 5.0 | 17.0 |
| C12-14 alpha olefin sulfonate | — | — | — | — | 6.0 |
| Coco amido propyl Amine Oxide | — | — | — | 1.0 | 5.0 |
| alkylpolyglucoside | — | 2.0 | — | — | — |
| C9-C11 alkyl EO8 ethoxylate | 5.0 | 4.0 | 8.0 | 4.0 | 3.0 |
| L-Glutamic acid-N,N-di(acetic acid) tetrasodium salt | 0.5 | — | — | — | — |
| dibenzyl (2S,2'S)-1,1'-(propane-1,3-diylbis(azanediyl))bis(1-oxo-3-phenylpropane-2,1-diyl)dicarbamate | 0.30 | 0.10 | 0.10 | 0.20 | 0.15 |

Minors and Balance with water up to 100%

TABLE 13

Hand-dish washing fluid detergent compositions comprising amido-gellants

| | Ex 5P | Ex 5Q | Ex 5R | Ex 5S | Ex 5T |
|---|---|---|---|---|---|
| Alkyl Ethoxy Sulfate AE2.0S | 17.0 | 12.0 | 24.0 | 18.0 | 29.0 |
| C12-14 alpha olefin sulfonate | — | — | 1.0 | — | — |
| Paraffin Sulfonate (C15) | 9.0 | 1.0 | 1.0 | — | — |
| Coco amido propyl amine oxide | — | 6.0 | — | — | 1.0 |
| Coco amido propyl Betaine | — | — | — | 5.0 | — |
| C12-C14 Akylpolyglucoside | — | 3.0 | 2.0 | — | — |
| C9-C11 alkyl EO8 ethoxylate | 8.0 | 2.0 | — | — | — |
| L-Glutamic acid-N,N-di(acetic acid) tetrasodium salt | 0.5 | — | 0.5 | — | — |
| Polypropylene glycol MW2000 | 1.0 | 1.0 | — | 0.5 | 0.5 |
| N,N'-(2S,2'S)-1,1'-(octane-1,8-diylbis(azanediyl))bis(3-methyl-1-oxobutane-2,1-diyl)dibenzamide | 0.10 | 0.15 | 0.10 | 0.20 | 0.15 |

Minors and Balance with water up to 100%

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern."

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A di-amido gellant having the following formula:

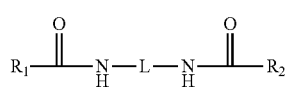

wherein:
L is an aliphatic linking group with a backbone chain of from 2 to 20 carbon atoms, having a molecular weight from 14 to 500 g/mol;

$R_1$ and $R_2$ both have the structure:

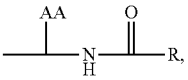

wherein:
AA is selected from the group consisting of:

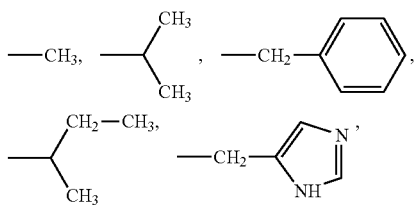

and R is selected from the group consisting of:

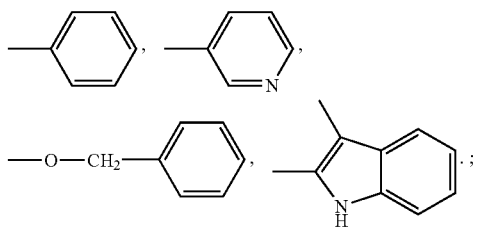

and the di-amido gellant is not a protein.

2. The di-amido gallant of claim 1, wherein the di-amido gellant has a molecular weight from 150 to 1500 g/mol.

3. The di-amido gallant of claim 1, wherein the di-amido gellant has a minimum gelling concentration (MGC) of from 0.1 to 100 mg/mL.

4. The di-amido gallant of claim 1, wherein the di-amido gellant is selected from the group consisting of: dibenzyl (2S,2'S)-1,1'-(ethane-1,2-diylbis(azanediyl))bis(3-methyl-1-oxobutane-2,1-diyl)dicarbamate; dibenzyl (2S,2'S)-1,1'-(propane-1,3-diylbis(azanediyl))bis(3-methyl-1-oxobutane-2,1-diyl)dicarbamate; dibenzyl (2S,2'S)-1,1'-(butane-1,4-diylbis(azanediyl))bis(3-methyl-1-oxobutane-2,1-diyl) dicarbamate; dibenzyl (2S,2'S)-1,1'-(pentane-1,5-diylbis(azanediyl))bis(3-methyl-1-oxobutane-2,1-diyl) dicarbamate; dibenzyl (2S,2'S)-1,1'-(hexane-1,6-diylbis(azanediyl))bis(3-methyl-1-oxobutane-2,1-diyl) dicarbamate; dibenzyl (2S,2'S)-1,1'-(heptane-1,7-diylbis(azanediyl))bis(3-methyl-1-oxobutane-2,1-diyl) dicarbamate; dibenzyl (2S,2'S)-1,1'-(octane-1,8-diylbis(azanediyl))bis(3-methyl-1-oxobutane-2,1-diyl) dicarbamate; dibenzyl (2S,2'S)-1,1'-(nonane-1,9-diylbis(azanediyl))bis(3-methyl-1-oxobutane-2,1-diyl) dicarbamate; dibenzyl (2S,2'S)-1,1'-(decane-1,10-diylbis(azanediyl))bis(3-methyl-1-oxobutane-2,1-diyl) dicarbamate; dibenzyl (2S,2'S)-1,1'-(undecane-1,1'-diylbis(azanediyl))bis(3-methyl-1-oxobutane-2,1-diyl) dicarbamate; dibenzyl (2S,2'S)-1,1'-(dodecane-1,12-diylbis(azanediyl))bis(3-methyl-1-oxobutane-2,1-diyl) dicarbamate; dibenzyl (2S,2'S)-1,1'-(tridecane-1,13-diylbis(azanediyl))bis(3-methyl-1-oxobutane-2,1-diyl) dicarbamate; dibenzyl (2S,2'S)-1,1'-(hexadecane-1,16-diylbis(azanediyl))bis(3-methyl-1-oxobutane-2,1-diyl)

dicarbamate; dibenzyl (2S,2'S)-1,1'-(octodecane-1,18-diyl-bis(azanediyl))bis(3-methyl-1-oxobutane-2,1-diyl)dicarbamate; dibenzyl (2S,2'S)-1,1'-(tetradecane-1,14-diylbis(azanediyl))bis(3-methyl-1-oxobutane-2,1-diyl)dicarbamate; N,N'-(2S,2'S)-1,1'-(ethane-1,2-diylbis(azanediyl))bis(3-methyl-1-oxobutane-2,1-diyl) dibenzamide; N,N'-(2S,2'S)-1,1'-(propane-1,3-diylbis(azanediyl))bis(3-methyl-1-oxobutane-2,1-diyl) dibenzamide; N,N'-(2S,2'S)-1,1'-(butane-1,4-diylbis(azanediyl))bis(3-methyl-1-oxobutane-2,1-diyl) dibenzamide; N,N'-(2S,2'S)-1,1'-(pentane-1,5-diylbis(azanediyl))bis(3-methyl-1-oxobutane-2,1-diyl) dibenzamide; N,N'-(2S,2'S)-1,1'-(hexane-1,6-diylbis(azanediyl))bis(3-methyl-1-oxobutane-2,1-diyl) dibenzamide; N,N'-(2S,2'S)-1,1'-(heptane-1,7-diylbis(azanediyl))bis(3-methyl-1-oxobutane-2,1-diyl) dibenzamide; N,N'-(2S,2'S)-1,1'-(octane-1,8-diylbis(azanediyl))bis(3-methyl-1-oxobutane-2,1-diyl) dibenzamide; N,N'-(2S,2'S)-1,1'-(nonane-1,9-diylbis(azanediyl))bis(3-methyl-1-oxobutane-2,1-diyl) dibenzamide; N,N'-(2S,2'S)-1,1'-(decane-1,10-diylbis(azanediyl))bis(3-methyl-1-oxobutane-2,1-diyl) dibenzamide; N,N'-(2S,2'S)-1,1'-(undecane-1,1'-diylbis(azanediyl))bis(3-methyl-1-oxobutane-2,1-diyl) dibenzamide; N,N'-(2S,2'S)-1,1'-(dodecane-1,12-diylbis(azanediyl))bis(3-methyl-1-oxobutane-2,1-diyl) dibenzamide; N,N'-(2S,2'S)-1,1'-(tridecane-1,13-diylbis(azanediyl))bis(3-methyl-1-oxobutane-2,1-diyl) dibenzamide; N,N'-(2S,2'S)-1,1'-(hexadecane-1,16-diylbis(azanediyl))bis(3-methyl-1-oxobutane-2,1-diyl) dibenzamide; N,N'-(2S,2'S)-1,1'-(octadecane-1,18-diylbis(azanediyl))bis(3-methyl-1-oxobutane-2,1-diyl) dibenzamide, N,N'-(2S,2'S)-1,1'-(tetradecane-1,14-diylbis(azanediyl))bis(3-methyl-1-oxobutane-2,1-diyl) dibenzamide; dibenzyl (2S,2'S)-1,1'-(ethane-1,2-diylbis(azanediyl))bis(1-oxopropane-2,1-diyl)dicarbamate; dibenzyl (2S,2'S)-1,1'-(propane-1,3-diylbis(azanediyl))bis(1-oxopropane-2,1-diyl)dicarbamate; dibenzyl (2S,2'S)-1,1'-(butane-1,4-diylbis(azanediyl))bis(1-oxopropane-2,1-diyl)dicarbamate; dibenzyl (2S,2'S)-1,1'-(pentane-1,5-diylbis(azanediyl))bis(1-oxopropane-2,1-diyl)dicarbamate; dibenzyl (2S,2'S)-1,1'-(hexane-1,6-diylbis(azanediyl))bis(1-oxopropane-2,1-diyl)dicarbamate; dibenzyl (2S,2'S)-1,1'-(heptane-1,7-diylbis(azanediyl))bis(1-oxopropane-2,1-diyl)dicarbamate; dibenzyl (2S,2'S)-1,1'-(octane-1,8-diylbis(azanediyl))bis(1-oxopropane-2,1-diyl)dicarbamate; dibenzyl (2S,2'S)-1,1'-(nonane-1,9-diylbis(azanediyl))bis(1-oxopropane-2,1-diyl)dicarbamate; dibenzyl (2S,2'S)-1,1'-(decane-1,10-diylbis(azanediyl))bis(1-oxopropane-2,1-diyl)dicarbamate; dibenzyl (2S,2'S)-1,1'-(undecane-1,1'-diylbis(azanediyl))bis(1-oxopropane-2,1-diyl)dicarbamate; dibenzyl (2S,2'S)-1,1'-(dodecane-1,12-diylbis(azanediyl))bis(1-oxopropane-2,1-diyl)dicarbamate; dibenzyl (2S,2'S)-1,1'-(tridecane-1,13-diylbis(azanediyl))bis(1-oxopropane-2,1-diyl)dicarbamate; dibenzyl (2S,2'S)-1,1'-(hexadecane-1,16-diylbis(azanediyl))bis(1-oxopropane-2,1-diyl)dicarbamate; dibenzyl (2S,2'S)-1,1'-(octadecane-1,18-diylbis(azanediyl))bis(1-oxopropane-2,1-diyl)dicarbamate; dibenzyl (2S,2'S)-1,1'-(tetradecane-1,14-diylbis(azanediyl))bis(1-oxopropane-2,1-diyl)dicarbamate; dibenzyl (2S,2'S)-1,1'-(ethane-1,2-diylbis(azanediyl))bis(1-oxo-3-phenylpropane-2,1-diyl)dicarbamate; dibenzyl (2S,2'S)-1,1'-(propane-1,3-diylbis(azanediyl))bis(1-oxo-3-phenylpropane-2,1-diyl)dicarbamate; dibenzyl (2S,2'S)-1,1'-(butane-1,4-diylbis(azanediyl))bis(1-oxo-3-phenylpropane-2,1-diyl)dicarbamate; dibenzyl (2S,2'S)-1,1'-(pentane-1,5-diylbis(azanediyl))bis(1-oxo-3-phenylpropane-2,1-diyl) dicarbamate; dibenzyl (2S,2'S)-1,1'-(hexane-1,6-diylbis(azanediyl))bis(1-oxo-3-phenylpropane-2,1-diyl)dicarbamate; dibenzyl (2S,2'S)-1,1'-(heptane-1,7-diylbis(azanediyl))bis(1-oxo-3-phenylpropane-2,1-diyl)dicarbamate; dibenzyl (2S,2'S)-1,1'-(nonane-1,9-diylbis(azanediyl))bis(1-oxo-3-phenylpropane-2,1-diyl)dicarbamate, dibenzyl (2S,2'S)-1,1'-(decane-1,10-diylbis(azanediyl))bis(1-oxo-3-phenylpropane-2,1-diyl)dicarbamate; dibenzyl (2S,2'S)-1,1'-(undecane-1,1'-diylbis(azanediyl))bis(1-oxo-3-phenylpropane-2,1-diyl)dicarbamate; dibenzyl (2S,2'S)-1,1'-(dodecane-1,12-diylbis(azanediyl))bis(1-oxo-3-phenylpropane-2,1-diyl)dicarbamate; dibenzyl (2S,2'S)-1,1'-(tridecane-1,13-diylbis(azanediyl))bis(1-oxo-3-phenylpropane-2,1-diyl)dicarbamate; dibenzyl (2S,2'S)-1,1'-(hexadecane-1,16-diylbis(azanediyl))bis(1-oxo-3-phenylpropane-2,1-diyl)dicarbamate; dibenzyl (2S,2'S)-1,1'-(octadecane-1,18-diylbis(azanediyl))bis(1-oxo-3-phenylpropane-2,1-diyl)dicarbamate; dibenzyl (2S,2'S)-1,1'-(tetradecane-1,14-diylbis(azanediyl))bis(1-oxo-3-phenylpropane-2,1-diyl)dicarbamate; N,N'-(2S,2'S)-1,1'-(nonane-1,9-diylbis(azanediyl))bis(1-oxo-3-phenylpropane-2,1-diyl)dibenzamide; N,N'-(2S,2'S)-1,1'-(decane-1,10-diylbis(azanediyl))bis(1-oxo-3-phenylpropane-2,1-diyl) dibenzamide; N,N'-(2S,2'S)-1,1'-(undecane-1,11-diylbis(azanediyl))bis(1-oxo-3-phenylpropane-2,1-diyl) dibenzamide; N,N'-(2S,2'S)-1,1'-(dodecane-1,12-diylbis(azanediyl))bis(1-oxo-3-phenylpropane-2,1-diyl) dibenzamide; N,N'-(2S,2'S)-1,1'-(tridecane-1,13-diylbis(azanediyl))bis(1-oxo-3-phenylpropane-2,1-diyl) dibenzamide; N,N'-(2S,2'S)-1,1'-(hexadecane-1,16-diylbis(azanediyl))bis(1-oxo-3-phenylpropane-2,1-diyl) dibenzamide; N,N'-(2S,2'S)-1,1'-(octadecane-1,18-diylbis(azanediyl))bis(1-oxo-3-phenylpropane-2,1-diyl) dibenzamide; N,N'-(2S,2'S)-1,1'-(tetradecane-1,14-diylbis(azanediyl))bis(1-oxo-3-phenylpropane-2,1-diyl) dibenzamide; N,N'(2S,2'S)-1,1'-(ethane-1,2-diylbis(azanediyl))bis(1-oxo-3-phenylpropane-2,1-diyl) dibenzamide; N,N'-(2S,2'S)-1,1'-(propane-1,3-diylbis(azanediyl))bis(1-oxo-3-phenylpropane-2,1-diyl) dibenzamide; N,N'-(2S,2'S)-1,1'-(butane-1,4-diylbis(azanediyl))bis(1-oxo-3-phenylpropane-2,1-diyl) dibenzamide; N,N'-(2S,2'S)-1,1'-(pentane-1,5-diylbis(azanediyl))bis(1-oxo-3-phenylpropane-2,1-diyl) dibenzamide; N,N'-(2S,2'S)-1,1'-(hexane-1,6-diylbis(azanediyl))bis(1-oxo-3-phenylpropane-2,1-diyl) dibenzamide; N,N'-(2S,2'S)-1,1'-(heptane-1,7-diylbis(azanediyl))bis(1-oxo-3-phenylpropane-2,1-diyl) dibenzamide; N,N'-(2S,2'S)-1,1'-(octane-1,8-diylbis(azanediyl))bis(1-oxo-3-phenylpropane-2,1-diyl) dibenzamide; N,N'-(2S,2'S)-1,1'-(ethane-1,2-diylbis(azanediyl))bis(1-oxopropane-2,1-diyl)dibenzamide; N,N'-(2S,2'S)-1,1'-(propane-1,3-diylbis(azanediyl))bis(1-oxopropane-2,1-diyl)dibenzamide; N,N'-(2S,2'S)-1,1'-(butane-1,4-diylbis(azanediyl))bis(1-oxopropane-2,1-diyl) dibenzamide; N,N'-(2S,2'S)-1,1'-(pentane-1,5-diylbis(azanediyl))bis(1-oxopropane-2,1-diyl)dibenzamide; N,N'-(2S,2'S)-1,1'-(hexane-1,6-diylbis(azanediyl))bis(1-oxopropane-2,1-diyl)dibenzamide; N,N'-(2S,2'S)-1,1'-(heptane-1,7-diylbis(azanediyl))bis(1-oxopropane-2,1-diyl) dibenzamide; N,N'-(2S,2'S)-1,1'-(octane-1,8-diylbis(azanediyl))bis(1-oxopropane-2,1-diyl)dibenzamide; N,N'-(2S,2'S)-1,1'-(nonane-1,9-diylbis(azanediyl))bis(1-oxopropane-2,1-diyl)dibenzamide; N,N'-(2S,2'S)-1,1'-(decane-1,10-diylbis(azanediyl))bis(1-oxopropane-2,1-diyl) dibenzamide; N,N'-(2S,2'S)-1,1'-(undecane-1,11-diylbis(azanediyl))bis(1-oxopropane-2,1-diyl)dibenzamide, N,N'-(2S,2'S)-1,1'-(dodecane-1,12-diylbis(azanediyl))bis(1- oxopropane-2,1-diyl)dibenzamide; N,N'-(2S,2'S)-1,1'-(tridecane-1,13-diylbis(azanediyl))bis(1-oxopropane-2,1-diyl)dibenzamide; N,N'-(2S,2'S)-1,1'-(hexadecane-1,16-diylbis(azanediyl))bis(1-oxopropane-2,1-diyl)dibenzamide; N,N'-(2S,2'S)-1,1'-(octadecane-1,18-diylbis(azanediyl))bis(1-oxopropane-2,1-diyl)dibenzamide; N,N'-(2S,2'S)-1,1'-(tetradecane-1,14-diylbis(azanediyl))bis(1-oxopropane-2,1-diyl)dibenzamide; dibenzyl (2S,2'S)-1,1'-(octane-1,8-diylbis(azanediyl))bis(1-oxo-3-phenylpropane-2,1-diyl) dicarbamate; {1-[2-(2-Benzyloxycarbonylamino-3-methyl-pentanoylamino)-ethylcarbamoyl]-2-methyl-butyl}-carbamic acid benzyl ester; {1-[8-(2-Benzyloxycarbonylamino-3-methyl-pentanoylamino)-octylcarbamoyl]-2-methyl-butyl}-carbamic acid benzyl ester; {1-[3-(2-Benzyloxycarbonylamino-3-methyl-pentanoylamino)-propylcarbamoyl]-2-methyl-butyl}-carbamic acid benzyl ester; {1-[9-(2-Benzyloxycarbonylamino-3-methyl-pentanoylamino)-nonylcarbamoyl]-2-methyl-butyl}-carbamic acid benzyl ester; {1-[4-(2-Benzyloxycarbonylamino-3-methyl-pentanoylamino)-butylcarbamoyl]-2-methyl-butyl}-carbamic acid benzyl ester; {1-[10-(2-Benzyloxycarbonylamino-3-methyl-pentanoylamino)-decylcarbamoyl]-2-methyl-butyl}-carbamic acid benzyl ester; {1-[5-(2-Benzyloxycarbonylamino-3-methyl-pentanoylamino)-pentylcarbamoyl]-2-methyl-butyl}-carbamic acid benzyl ester; {1-[711(2-Benzyloxycarbonylamino-3-methyl-pentanoylamino)-undecylcarbamoyl]-2-methyl-butyl}-carbamic acid benzyl ester; {1-[6-(2-Benzyloxycarbonylamino-3-methyl-pentanoylamino)-hexylcarbamoyl]-2-methyl-butyl}-carbamic acid benzyl ester; {1-[12-(2-Benzyloxycarbonylamino-3-methyl-pentanoylamino)-dodecylcarbamoyl]-2-methyl-butyl}-carbamic acid benzyl ester; {1-[7-(2-Benzyloxycarbonylamino-3-methyl-pentanoylamino)-heptylcarbamoyl]-2-methyl-butyl}-carbamic acid benzyl ester; (1-Benzyl-2-{2-[2-(9H-fluoren-9-yloxycarbonylamino)-3-phenyl-propionylamino]-ethylamino}-ethyl)-carbamic acid 9H-fluoren-9-yl ester; (1-Benzyl-2-{8-[2-(9H-fluoren-9-yloxycarbonylamino)-3-phenyl-propionylamino]-octylamino}-ethyl)-carbamic acid 9H-fluoren-9-yl ester; (1-Benzyl-2-{3-[2-(9H-fluoren-9-yloxycarbonylamino)-3-phenyl-propionylamino]-propylamino}-ethyl)-carbamic acid 9H-fluoren-9-yl ester; (1-Benzyl-2-{9-[2-(9H-fluoren-9-yloxycarbonylamino)-3-phenyl-propionylamino]-nonylamino}-ethyl)-carbamic acid 9H-fluoren-9-yl ester; (1-Benzyl-2-{4-[2-(9H-fluoren-9-yloxycarbonylamino)-3-phenyl-propionylamino]-butylamino}-ethyl)-carbamic acid 9H-fluoren-9-yl ester; (1-Benzyl-2-{10-[2-(9H-fluoren-9-yloxycarbonylamino)-3-phenyl-propionylamino]-decylamino}-ethyl)-carbamic acid 9H-fluoren-9-yl ester; (1-Benzyl-2-{5-[2-(9H-fluoren-9-yloxycarbonylamino)-3-phenyl-propionylamino]-pentylamino}-ethyl)-carbamic acid 9H-fluoren-9-yl ester; (1-Benzyl-2-{11-[2-(9H-fluoren-9-yloxycarbonylamino)-3-phenyl-propionylamino]-undecylamino}-ethyl)-carbamic acid 9H-fluoren-9-yl ester; (1-Benzyl-2-{6-[2-(9H-fluoren-9-yloxycarbonylamino)-3-phenyl-propionylamino]-hexylamino}-ethyl)-carbamic acid 9H-fluoren-9-yl ester; (1-Benzyl-2-{12-[2-(9H-fluoren-9-yloxycarbonylamino)-3-phenyl-propionylamino]-dodecylamino}-ethyl)-carbamic acid 9H-fluoren-9-yl ester; (1-Benzyl-2-{7-[2-(9H-fluoren-9-yloxycarbonylamino)-3-phenyl-propionylamino]-heptylamino}-ethyl)-carbamic acid 9H-fluoren-9-yl ester; tert-butyl N-[(1S)-1-benzyl-2-[2-[[(2S)-2-(tert-butoxycarbonylamino)-3-phenyl-propanoyl]amino]ethylamino]-2-oxo-ethyl]carbamate; tert-butyl N-[(1S)-1-benzyl-2-[8-[[(2S)-2-(tert-butoxycarbonylamino)-3-phenyl-propanoyl]amino]octylamino]-2-oxo-ethyl]carbamate; tert-butyl N-[(1S)-1-benzyl-2-[3-[[(2S)-2-(tert-butoxycarbonylamino)-3-phenyl-propanoyl]amino]propylamino]-2-oxo-ethyl]carbamate; tert-butyl N-[(1S)-1-benzyl-2-[9-[[(2S)-2-(tert-butoxycarbonylamino)-3-phenyl-propanoyl]amino]nonylamino]-2-oxo-ethyl]carbamate; tert-butyl N-[(1S)-1-benzyl-2-[4-[[(2S)-2-(tert-butoxycarbonylamino)-3-phenyl-propanoyl]amino]butylamino]-2-oxo-ethyl]carbamate; tert-butyl N-[(1S)-1-benzyl-2-[10-[[(2S)-2-(tert-butoxycarbonylamino)-3-phenyl-propanoyl]amino]decylamino]-2-oxo-ethyl]carbamate; tert-butyl N-[(1S)-1-benzyl-2-[5-[[(2S)-2-(tert-butoxycarbonylamino)-3-phenyl-propanoyl]amino]pentylamino]-2-oxo-ethyl]carbamate; tert-butyl N-[(1S)-1-benzyl-2-[11-[[(2S)-2-(tert-butoxycarbonylamino)-3-phenyl-propanoyl]amino]undecylamino]-2-oxo-ethyl]carbamate; tert-butyl N-[(1S)-1-benzyl-2-[6-[[(2S)-2-(tert-butoxycarbonylamino)-3-phenyl-propanoyl]amino]hexylamino]-2-oxo-ethyl]carbamate; tert-butyl N-[(1S)-1-benzyl-2-[12-[[(2S)-2-(tert-butoxycarbonylamino)-3-phenyl-propanoyl]amino]dodecylamino]-2-oxo-ethyl]carbamate; tert-butyl N-[(1S)-1-benzyl-2-[7-[[(2S)-2-(tert-butoxycarbonylamino)-3-phenyl-propanoyl]amino]heptylamino]-2-oxo-ethyl]carbamate; and mixtures thereof.

* * * * *